United States Patent [19]
Hoffman et al.

[11] Patent Number: 5,814,617
[45] Date of Patent: Sep. 29, 1998

[54] PROTECTIVE 17 KDA MALARIA HEPATIC AND ERYTHROCYTIC STAGE IMMUNOGEN AND GENE

[75] Inventors: Stephen L. Hoffman, Gaithersburg; Yupin Charoenvit, Silver Spring; Richard C. Hedstrom, Gaithersburg; Denise L. Doolan, Rockville, all of Md.

[73] Assignee: The United States of America as represented by the Secretary of the Navy, Washington, D.C.

[21] Appl. No.: 319,704

[22] Filed: Oct. 7, 1994

[51] Int. Cl.⁶ ........................ A61K 31/505; C07K 14/445
[52] U.S. Cl. ........................ 514/44; 536/23.5; 424/268.1; 424/272.1; 530/350; 530/395
[58] Field of Search ............................... 536/23.5; 514/44; 424/268.1, 272.1; 530/350, 395

[56] References Cited

PUBLICATIONS

Hope st al., "The gene for an exported antigen of the malaria *Plasmodium falciparum* cloned and expressed in *Escheruchia coli*" Nucleic Acids Research, vol. 13, No. 2, 1985.

Caspers et al., "A *Plasmodium falciparum* malaria vaccine candidate which contains epitopes from the circumsorozoite protein and a blood stage antigen, 5.1" Molecular and Biochemical Parasitology, 47, pp. 143–150 (1991).

Stürchler et al., "Evaluation of 5.1–[NANP]₁₉, A Recombinant *Plasmodium falciparum* Vaccine Candidate in Adults" Trop. Geogr. Med 44 pp. 9–14 (1992).

Sanchez et al., "*Plasmodium falciparum*: Exported Protein–1, a Blood Stage Antigen is Expressed in Liver Stage Parasites" Experimental Parasitology 79, 59–62 (1994).

Hope et al., "Evidence for Immunological Cross–reaction Between Sporozoites and Blood Stages of a Human Malaria Parasite" Nature, vol. ??, pp. 191–194 (1??4)(1994?).

Doolan et al., "Circumventing Genetic Restrictions of Protection Against Malaria with Multi–Gene DNA Immunizatio: CD8+ T Cell, Interferon–γ, and Nitric Oxide Dependent Immunity" J. Exp Med (in press).

Doolan et al., "Characterization of the Protective *Hepatocyte Erythrocyte* Protein 17 kDa Gene of *Plasmodium Yoelli*: Homolog of *Plasmodium Falciparum* Exported Protein 1" (submitted for publication).

*Primary Examiner*—Thomas M. Cunningham
*Attorney, Agent, or Firm*—A. David Spevack

[57] ABSTRACT

An IgG1 monoclonal antibody, Navy *Yoelii* Liver Stage 3 (NYLS3) does not recognize sporozoites, but recognizes *P. yoelii* liver stage parasites within 6 hours of invasion of mouse hepatocytes, and throughout the hepatic and asexual erythrocytic stages of the life cycle. When added to primary cultures of mouse hepatocytes 24 hours after inoculation with *P. yoelii* sporozoites, when all sporozoites have invaded hepatocytes, NYLS3 eliminates up to 98% of liver stage parasites. Intravenous injection of NYLS3 into mice delays the onset and reduces the density of blood stage parasitemia after sporozoite or blood stage challenge. The protein recognized by this mAb is identified and designated *P. yoelii* hepatic and erythrocytic stage protein, 17-kDa or PyHEP17. The gene encoding PyHEP17 and a DNA vaccine comprising exons of the DNA that encodes PyHEP17 are disclosed. A DNA vaccine consisting of exon 1 and part of exon 2 of the gene encoding PyHEP17 protects 86% of A/J mice, 33%–43% of B10.BR mice, 17%–29% of BALB/c mice and 14%–20% of B10.Q mice from development of blood-stage parasitemia. A combination of DNA vaccines consisting of a PyHEP17 DNA vaccine and a PyCSP DNA vaccine confers complete protection against development of blood-stage parasitemia in BALB/c mice and 71% protection in A/J and B10.BR mice. This DNA vaccine-induced protection may be additive. Combinations of other malaria antigens are covered. The application discloses the *P. falciparum* homolog of PyHEP17 and includes the means of identification of the PyHEP17 homologs of the other Plasmodium species which infect humans, specifically *P. vivax*, *P. ovale* and *P. malariae*.

11 Claims, 7 Drawing Sheets

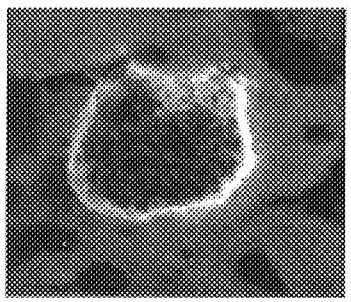
FIG. 2A
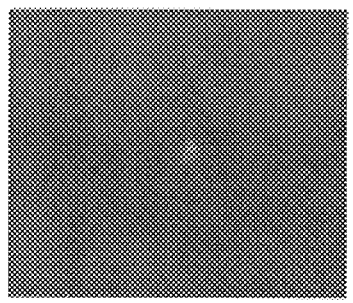
FIG. 2B
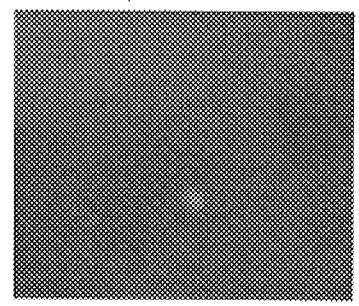
FIG. 2C
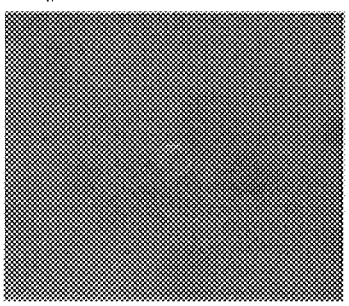
FIG. 2D
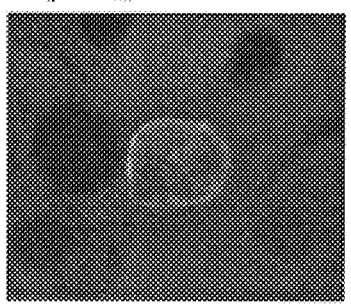
FIG. 2E
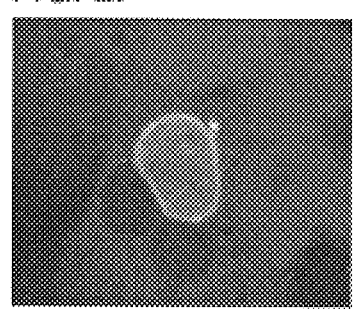
FIG. 2F
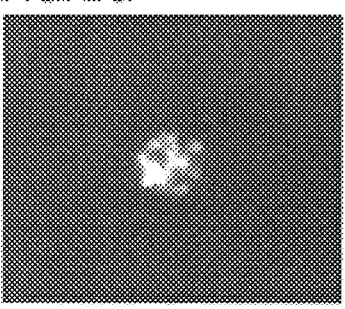
FIG. 2G
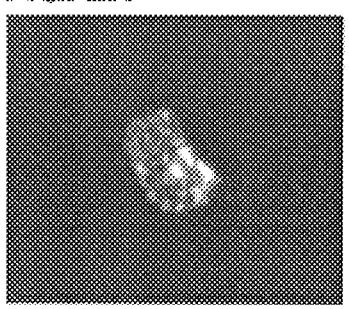
FIG. 2H
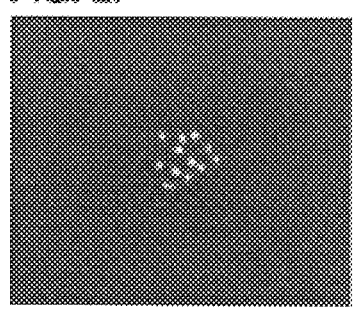
FIG. 2I
FIG. 2
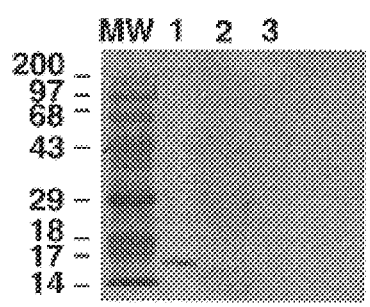
FIG. 3

FIG. 4A
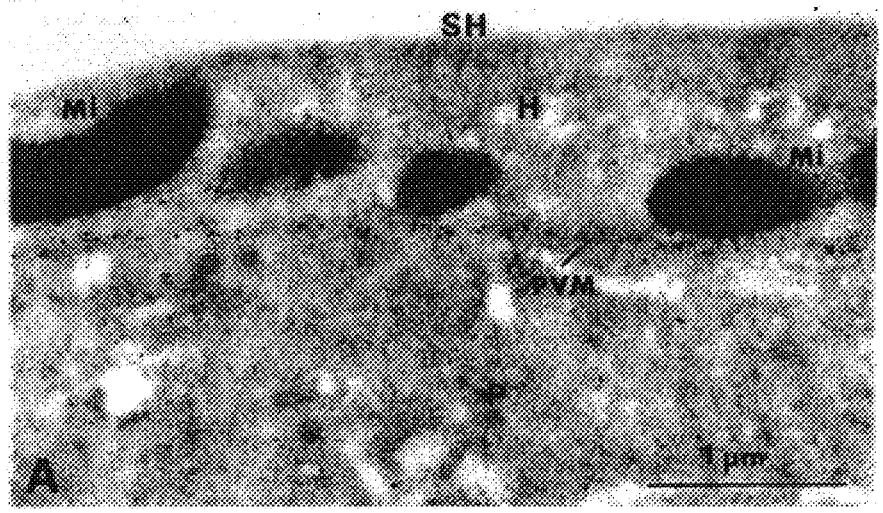
FIG. 4B
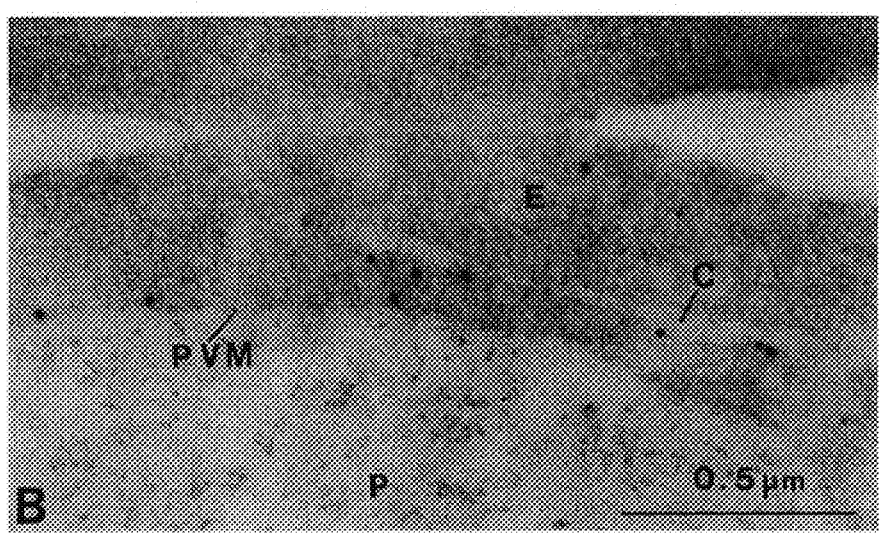
FIG. 4

```
PfExp1 cDNA    MKILSVFFLA LFFIIFNKES LAEKTNKET- G-SGVSSKKK NKKGSGEPLI    48
Lisa3 cDNA     MKI-NI--AS IIFIIFSLCL VNDAYGKNKY GKNGKYGSQN VIKKHGEPVI    47
Consensus      MKI....... ..FIIF.... ......K... G..G...... ..K..GEP.I    50

PfExp1 cDNA    DVHDLISDMI KKEEELVEVN KRKSKYKLAT SVLAGLLGVV STVLLGGVGL    98
Lisa3 cDNA     NVQDLISDMV RKEEEIVKLT KNKKSLRKIN VALATALSVV SAILLGGAGL    97
Consensus      .V.DLISDM. .KEEE.V... K.K....... ..LA..L.VV S..LLGG.GL   100

PfExp1 cDNA    VLYNTEKGRH PFKIGSSDPA DNANPDADSE SNGEPNADPQ VTAQDVTPEQ   148
Lisa3 cDNA     VMYNTEKGRR PFQIGKS--- ---------- ---------- ----------   114
Consensus      V.YNTEKGR. PF.IG.S... .......... .......... ..........   150

PfExp1 cDNA    PQGDDNNLVS GPEH                                           162
Lisa3 cDNA     ---------- ----                                           114
Consensus      .......... ....                                           164
```

FIG. 7

```
         10         20         30         40         50         60
1234567890 1234567890 1234567890 1234567890 1234567890 1234567890
ATGAAAATCA ATATAGCTTC AATTATTTTT ATTATCTTTT CTCTTTGCCT TGTTAATGAT    60
 M  K  I  N  I  A  S  I  I  F  I  I  F  S  L  C  L  V  N  D

GCTTATGGAA AAAACAAGTA TGGTAAAAAT GGCAAATATG GCTCCCAAAA TGTTATTAAG   120
 A  Y  G  K  N  K  Y  G  K  N  G  K  Y  G  S  Q  N  V  I  K

AAACACGGAG AACCCGTAAT TAATGTACAA GACTTAATTA GCGACATGGT TAGGAAAGAA   180
 K  H  G  E  P  V  I  N  V  Q  D  L  I  S  D  M  V  R  K  E

GAAGAAATTG TTAAAATTGAC AAAAAAATAAA AAATCTTTAA CGTAGCTCTT            240
 E  E  I  V  K  L  T  K  N  K  K  S  L  R  K  I  N  V  A  L

GCCACAGCAT TAAGTGTTGT ATCAGCAATA TTACTTGGAG GTGCTGGATT AGTTATGTAC   300
 A  T  A  L  S  V  V  S  A  I  L  L  G  G  A  G  L  V  M  Y

AATACTGAAA AGGGAAGACG CCCATTTCAA ATTGGCAAAT CA                      342
 N  T  E  K  R  G  R  R  P  F  Q  I  G  K  S
```

FIG. 8

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

Ser Phe Pro Met Asn Glu Glu Ser Pro Leu Gly Phe Ser Pro Glu
    1               5                        10                   15

( 2 ) INFORMATION FOR SEQ ID NO:2:

( i ) SEQUENCE CHARACTERISTICS:
   ( A ) LENGTH: 15 amino acids
   ( B ) TYPE: amino acid
   ( D ) TOPOLOGY: linear ( i i ) MOLECULE TYPE: peptide ( x i ) SEQUENCE DESCRIPTION: SEQ ID NO:2:

| Glu | Glu | Ser | Pro | Leu | Gly | Phe | Ser | Pro | Glu | Glu | Met | Glu | Ala | Val |
|-----|-----|-----|-----|-----|-----|-----|-----|-----|-----|-----|-----|-----|-----|-----|
| 1   |     |     |     | 5   |     |     |     |     | 10  |     |     |     |     | 15  |

( 2 ) INFORMATION FOR SEQ ID NO:3:

( i ) SEQUENCE CHARACTERISTICS:
      ( A ) LENGTH: 114 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:3:

| Met | Lys | Ile | Asn | Ile | Ala | Ser | Ile | Ile | Phe | Ile | Ile | Phe | Ser | Leu | Cys |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Leu | Val | Asn | Asp | Ala | Tyr | Gly | Lys | Asn | Lys | Tyr | Gly | Lys | Asn | Gly | Lys |
|     |     |     | 20  |     |     |     |     | 25  |     |     |     |     | 30  |     |     |

| Tyr | Gly | Ser | Gln | Asn | Val | Ile | Lys | Lys | His | Gly | Glu | Pro | Val | Ile | Asn |
|     |     |     | 35  |     |     |     |     | 40  |     |     |     |     | 45  |     |     |

| Val | Gln | Asp | Leu | Ile | Ser | Asp | Met | Val | Arg | Lys | Glu | Glu | Glu | Ile | Val |
|     |     | 50  |     |     |     |     | 55  |     |     |     |     | 60  |     |     |     |

| Lys | Leu | Thr | Lys | Asn | Lys | Lys | Ser | Leu | Arg | Lys | Ile | Asn | Val | Ala | Leu |
| 65  |     |     |     |     | 70  |     |     |     |     | 75  |     |     |     |     | 80  |

| Ala | Thr | Ala | Leu | Ser | Val | Val | Ser | Ala | Ile | Leu | Leu | Gly | Gly | Ala | Gly |
|     |     |     |     | 85  |     |     |     |     | 90  |     |     |     |     | 95  |     |

| Leu | Val | Met | Tyr | Asn | Thr | Glu | Lys | Gly | Arg | Arg | Pro | Phe | Gln | Ile | Gly |
|     |     |     | 100 |     |     |     |     | 105 |     |     |     |     | 110 |     |     |

| Lys | Ser |
|-----|-----|

( 2 ) INFORMATION FOR SEQ ID NO:4:

( i ) SEQUENCE CHARACTERISTICS:
      ( A ) LENGTH: 342 base pairs
      ( B ) TYPE: nucleic acid
      ( C ) STRANDEDNESS: single
      ( D ) TOPOLOGY: linear ( i i ) MOLECULE TYPE: protein ( x i ) SEQUENCE DESCRIPTION: SEQ ID NO:4:

```
ATGAAAATCA ATATAGCTTC AATTATTTTT ATTATCTTTT CTCTTGCCTT GTTAATGATG      60
CTTATGGAAA AAACAAGTAT GGTAAAAATG GCAAATATGG CTCCCAAAAT GTTATTAAGA     120
AAACACGGAG AACCCGTAAT TAATGTACAA GACTTAATTA GCGACATGGT TAGGAAAGAA     180
GAAGAAATTG TTAAATTGAC AAAAAATAAA AAATCTTTAA GAAAAATAAA CGTAGCTCTT     240
GCCACAGCAT TAAGTGTTGT ATCAGCAATA TTACTTGGAG GTGCTGGATT AGTTATGTAC     300
AATACTGAAA AGGGAAGACG CCCATTTCAA ATTGGCAAAT CA                        342
```

( 2 ) INFORMATION FOR SEQ ID NO:5:

( i ) SEQUENCE CHARACTERISTICS:
      ( A ) LENGTH: 1422 base pairs
      ( B ) TYPE: nucleic acid
      ( C ) STRANDEDNESS: single 5,814,617

27 28

-continued ( D ) TOPOLOGY: linear ( i i ) MOLECULE TYPE: DNA (genomic)

( x i ) SEQUENCE DESCRIPTION: SEQ ID NO:5:

| ATTAAATCAT | ATATGATATA | TTATAGTGCA | CATATGGCAC | TATATTTTCT | AAAAAAATTA | 60 |
| TATTTTAATA | TAGTTAGCGA | GATTTAAAAA | ATAATTATTT | TATTGGATAA | ATTTATAGCA | 120 |
| TAGATTATTA | TCTCTATATA | GAAAAAATAT | TAAAAAAATA | TTTTTATAAT | CTTTTATAAA | 180 |
| TTTTAATTTT | TATTATTAAT | TTTGTATGAA | AATAATATTT | ATATTTTCT | AGAATTTAAA | 240 |
| TTTTTAATAA | AATATTATTA | ATTCAATAAT | AATTAAAAAT | TTATTTTATT | AATTCAATTA | 300 |
| TAATCCAATA | TAAGCATATA | ATTTAAGATT | TTCTTCAAAG | TATATATCTT | TATTTTAATC | 360 |
| TTAAACTTTT | CTTGAAAATG | AAAATCAATA | TAGCTTCAAT | TATTTTTATT | ATCTTTTCTC | 420 |
| TTTGCCTTGT | TAATGATGCT | TATGGAAAAA | ACAAGTATGG | TAAAAATGGC | AAATATGGCT | 480 |
| CCCAAAATGT | TATTAAGAGT | AAGTTGATTT | AAAGTAATAT | ATACTAATTT | AAGTATCCAT | 540 |
| ATATACATGT | TTATACTTTT | GAGTTATACG | TAATGTATAA | TACGAAACTT | GTATTTAATA | 600 |
| TTTTAAAAAA | CAAAATGAGG | GGGGAGATGC | TTATTATTAC | ATTCTCACAT | TAATCTCTTC | 660 |
| GTTCATCCAT | TACTTGTTTA | TAGCCCACTA | AACACATTTA | TTTACCTGCT | TATTTATTTA | 720 |
| TTATTTATTT | ATTATTTATT | TATTATTTAC | TCACTTTTTA | ATAATTTGTT | TAGAACACGG | 780 |
| AGAACCCGTA | ATTAATGTAC | AAGACTTAAT | TAGCGACATG | GTTAGGAAAG | AAGAAGAAAT | 840 |
| TGTTAAATTG | ACAAAAAATA | AAAAATCTTT | AAGAAAAATA | AACGTAGCTC | TTGCCACAGC | 900 |
| ATTAAGTGTT | GTATCAGCAA | TATTACTTGG | AGGTGCTGGA | TTAGTTATGT | ACAATACTGA | 960 |
| AAAGGGAAGA | CGCCCATTTC | AAATTGGCAA | ATCAAAAAG | GGAGGATCTG | CAATGGCTCG | 1020 |
| AGACTCTTCC | TTTCCAATGA | ATGAGGAATC | ACCCTTAGGT | TTTTCACCCG | AAGAAATGGA | 1080 |
| AGCAGTTGCT | TCTAAGTTCA | GAGAAGTATG | TTAAAGATGG | AGTGCCTGCA | CATCTAACAC | 1140 |
| CCCAAATGTT | CAAAACTGAA | GTAATTGGAT | TTTAGTATCA | TAAAAAGTTT | CGACTCTAAA | 1200 |
| TAAATTGAAT | TTCCGAATAA | TATAAATTTT | TAAAAATTTC | ATTAGAATTA | TAAACATAAT | 1260 |
| ATAAAATGTT | CTGAACGATT | ATATATTATG | TTCTTTTCTT | AGAAATATAC | TATGAAAATA | 1320 |
| ATTGAATTTA | TATTATAAGT | TTTTTTTTTT | TTTTTTTTAT | TATCCCATGG | CATAATACAT | 1380 |
| GCCTTTGTTC | TACTTGTTAA | TTTTTTTTTT | TATTATTTCA | TG | | 1422 |

( 2 ) INFORMATION FOR SEQ ID NO:6:

( i ) SEQUENCE CHARACTERISTICS:
        ( A ) LENGTH: 162 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

| Met | Lys | Ile | Leu | Ser | Val | Phe | Phe | Leu | Ala | Leu | Phe | Phe | Ile | Ile | Phe |
| 1 | | | | 5 | | | | | 10 | | | | | 15 | |
| Asn | Lys | Glu | Ser | Leu | Ala | Glu | Lys | Thr | Asn | Lys | Glu | Thr | Gly | Ser | Gly |
| | | | 20 | | | | | 25 | | | | | 30 | | |
| Val | Ser | Ser | Lys | Lys | Lys | Asn | Lys | Lys | Gly | Ser | Gly | Glu | Pro | Leu | Ile |
| | | 35 | | | | | 40 | | | | | 45 | | | |
| Asp | Val | His | Asp | Leu | Ile | Ser | Asp | Met | Ile | Lys | Lys | Glu | Glu | Glu | Leu |
| | 50 | | | | | 55 | | | | | 60 | | | | |
| Val | Glu | Val | Asn | Lys | Arg | Lys | Ser | Lys | Tyr | Lys | Leu | Ala | Thr | Ser | Val |
| 65 | | | | | 70 | | | | | 75 | | | | | 80 |

```
        Leu   Ala   Gly   Leu   Leu   Gly   Val   Val   Ser   Thr   Val   Leu   Leu   Gly   Gly   Val
                          85                            90                                  95

Gly   Leu   Val   Leu   Tyr   Asn   Thr   Glu   Lys   Gly   Arg   His   Pro   Phe   Lys   Ile
                          100                           105                                 110

Gly   Ser   Ser   Asp   Pro   Ala   Asp   Asn   Ala   Asn   Pro   Asp   Ala   Asp   Ser   Glu
                    115                           120                           125

Ser   Asn   Gly   Glu   Pro   Asn   Ala   Asp   Pro   Gln   Val   Thr   Ala   Gln   Asp   Val
              130                           135                           140

Thr   Pro   Glu   Gln   Pro   Gln   Gly   Asp   Asp   Asn   Asn   Leu   Val   Ser   Gly   Pro
        145                           150                           155                           160

Glu   His
```

( 2 ) INFORMATION FOR SEQ ID NO:7:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

GGAATTCATG AAAATCAATA TAGC                                              24

( 2 ) INFORMATION FOR SEQ ID NO:8:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

GGGATCCTGA TTTGCCAATT TGAAA                                           25

( 2 ) INFORMATION FOR SEQ ID NO:9:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:9:

```
        Glu   Glu   Ser   Pro   Leu   Gly   Phe   Ser   Pro   Glu
        1                       5                             10
```

( 2 ) INFORMATION FOR SEQ ID NO:10:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:10:

```
        Gln   Tyr   Ile   Lys   Ala   Asn   Ser   Lys   Phe   Ile   Gly   Ile   Thr   Glu   Leu
        1                       5                             10                          15
```

( 2 ) INFORMATION FOR SEQ ID NO:11:

(  i  ) SEQUENCE CHARACTERISTICS:
  (  A  ) LENGTH: 20 amino acids
  (  B  ) TYPE: amino acid
  (  D  ) TOPOLOGY: linear (  i i  ) MOLECULE TYPE: peptide (  x i  ) SEQUENCE DESCRIPTION: SEQ ID NO:11:

```
Phe  Asn  Asn  Phe  Thr  Val  Ser  Phe  Trp  Leu  Arg  Val  Lys  Val  Ser  Ala
1                   5                        10                       15

Ser  His  Leu  Glu
               20
```

PROTECTIVE 17 KDA MALARIA HEPATIC AND ERYTHROCYTIC STAGE IMMUNOGEN AND GENE

BACKGROUND OF THE INVENTION

FIELD OF THE INVENTION

This invention relates to a gene encoding a malaria protein, monoclonal antibodies specific for the protein, and vaccines for protection against malaria in humans.

INTRODUCTION

Prevention of infection by human malaria parasites would alleviate a major health problem in the tropical and sub-tropical areas of the world. The World Health Organization estimates that 300 to 500 million cases of clinical malaria occur each year, resulting in up to 2.7 million deaths (Nussenzweig et al). The most promising method for the control of malaria appears to be the development and use of vaccines.

Species of the genus Plasmodium are the etiological agents of malaria. These protozoan parasites have a complex life cycle involving reproduction in mammalian hosts and insect vectors. The principal infectious stage of the parasite is called the sporozoite.

The sporozoite is inoculated into a mammalian host by the bite of infected Anopheles species mosquitoes. After inoculation, sporozoites rapidly make their way to the liver, where a single, uninucleate sporozoite develops during a minimum of 5–6 days into a mature liver schizont with $1-3 \times 10^4$ uninucleate merozoites. The schizonts emerge into the bloodstream and enter red blood cells where they multiply, rupturing the cells and emerging as merozoites to invade other red blood cells (FIG. 1).

There are no clinical or pathological manifestations associated with the liver stage of the malaria parasite's life cycle. Thus, the parasite developing within the liver is an attractive target for vaccine-induced protective immune responses.

Several species of Plasmodium cause malaria in humans: these include *P. falciparum, P. vivax, P. ovale* and *P. malariae*. Another species, *P. yoelii*, causes malaria in rodents and has been used as a model system in vaccine research. This use has included successful identification of target antigens for vaccine development.

The infected hepatocyte is an important target of malaria vaccine-induced protective immune responses (Hoffman et al, 1989, 1993). Cytotoxic T lymphocytes (CTL) against the circumsporozoite proteins (CSP) of *P. yoelii* (Rodrigues et al.; Weiss et al.) and *P. berghei* (Romero et al.), and CTL against the *P. yoelii* sporozoite surface protein 2 (SSP2) (Khusmith et al.) have been shown to completely protect against sporozoite-induced malaria. Two other liver stage antigens have been identified, a *P. falciparum* liver stage antigen-1 (LSA-1) (Guerin-Marchand et al.; Zhu et al.) and a *P. berghei* protein designated Pbl-1 (Sinden et al.). In addition, a number of blood stage antigens including the *P. falciparum* merozoite surface protein (MSP-1) (Szarfman et al.) and the *P. falciparum* exported protein-1 (EXP1) (Sanchez et al.) are first expressed in infected hepatocytes.

It is important to recognize other antigens expressed in infected hepatocytes as targets for human vaccine development. It is also important to isolate the genes encoding these identified antigens. The genes can be used to construct DNA vaccines, and can also be used to produce by recombinant techniques proteins resembling the native protein and derivatives thereof for use as vaccines.

SUMMARY OF THE INVENTION

This invention is directed to a monoclonal antibody that recognizes *P. yoelii* liver stage parasites, use of the antibody to treat malaria infection in mammals, and use of the antibody for diagnostic purposes.

This invention also relates to a protein, *Plasmodium yoelii* Hepatocyte Erythrocyte Protein 17 (PyHEP17), expressed by *P. yoelii* during the hepatic and erythrocytic stages of malaria infection, and to homologs of this protein from Plasmodium species that infect humans. These include *P. falciparum, P. vivax, P. ovale* and *P. malariae*.

This invention also relates to use of the PyHEP17 gene sequences to identify homologs of PyHEP17 from the Plasmodium species that infect humans.

The invention further relates to derivatives of PyHEP17 and its homologs, and use of these proteins and their derivatives as vaccines against malaria infection in mammals.

Another aspect of this invention relates to DNA and cDNA encoding PY/HEP17 and its homologs, and to parts of the DNA and cDNA, and to the use of these DNAs as vaccines against malaria infection in mammals.

This aspect of the invention also relates to the use of this DNA or cDNA to express recombinant PyHEP17 and its homologs and fragments thereof, and use of the proteins and fragments as combination vaccines with the DNA vaccine of the invention.

This invention further relates to synthetic peptides based on the deduced amino acid sequences of PyHEP17 and its homologs, and use of these synthetic peptides as combination vaccines with the DNA vaccine of the invention.

Yet another aspect of this invention relates to modifications of the genes encoding PyHEP17 and its homologs, to produce proteins sharing some characteristics of PyHEP17 and its homologs, and having use as vaccines against malaria in mammals.

BRIEF DESCRIPTION OF THE DRAWINGS

A more complete appreciation of the invention will be obtained by reference to the following description of the preferred embodiments and the accompanying drawings.

FIG. 2 is a series of digitized, computer produced images of original micrographs which show NYLS3 recognition of infected hepatocytes and erythrocytes by indirect fluorescent antibody testing (IFAT).

FIG. 2A An infected hepatocyte in a section of liver taken 44 hours after inoculation of a mouse with *P. yoelii* sporozoites;

FIG. 2B An infected hepatocyte from a primary culture of mouse hepatocytes 72 hours after inoculation with radiation attenuated sporozoites;

FIG. 2C Infected hepatocytes in primary cultures, 6 hours after inoculation with non-irradiated sporozoites.

FIG. 2D Infected hepatocyte in primary cultures 24 hours after inoculation with non-irradiated sporozoites.

FIG. 2E Infected hepatocyte in primary cultures 48 hours after inoculation with non-irradiated sporozoites.

FIG. 2F Infected hepatocyte in primary cultures 72 hours after inoculation with non-irradiated sporozoites.

FIG. 2G erythrocytes infected with developing schizonts. Magnifications: A–F:×400 and G–I:×1000.

FIG. 2H erythrocytes infected with mature schizonts. Magnifications: A–F:×400 and G–I:×1000.

FIG. 2I Free merozoites after rupture of infected erythrocytes. Magnifications: A–F:×400 and G–I:×1000.

FIG. 3 is a digitized image of a western blot which shows recognition by NYLS3 of a 17-kDa protein (PyHEP17) by Western blot analysis of an extract of P. yoelii-infected erythrocytes. Extracts were prepared from P. yoelii infected mouse erythrocytes (lane 1), uninfected mouse erythrocytes (lane 2), and P. yoelii sporozoites (lane 3). The extracts were separated by SDS/PAGE in a 12% polyacrylamide gel. Protein bands were transferred onto nitrocellulose and stained by incubation with NYLS3 and HRP-labeled goat anti-mouse IgG, and revealed by incubating with a substrate solution (4-chloro-1-napthol+$H_2O_2$). NYLS3 identified a 17-kDa protein in the extract of infected erythrocytes (lane 1). The sizes of protein m.w. standards (in kDa) are shown at the far left.

FIG. 4 is a series of digitized electron micrographs, which shows localization of PyHEP17 by immunoelectron microscopy.

FIG. 4A P. yoelii-infected hepatocyte 72 hours after inoculation of a primary culture. SH, surface of hepatocyte; H, hepatocyte; PVM, parasitophorous vacuole membrane; Mi, mitochondria; P, parasite, Bar=1 μm.

FIG. 4B Erythrocyte infected with a P. yoelii trophozoite. E, erythrocyte; C, cleft; PVM, parasitophorous vacuole membrane; P, parasite, Bar=0.5 μm.

FIG. 7 shows the amino acid sequence homology between the derived amino acid sequence shown in FIG. 8 and the corresponding region of the Exp1 antigen of P. falciparum (PfExp1) (SEQ ID NO: 6).

FIG. 8 shows the DNA sequence of clone pUC18/LisaEx1.2 (SEQ ID NO: 4) and the derived amino acid sequence (SEQ ID NO: 3).

DESCRIPTION OF THE PREFERRED EMBODIMENTS

Introduction

Figure 1:
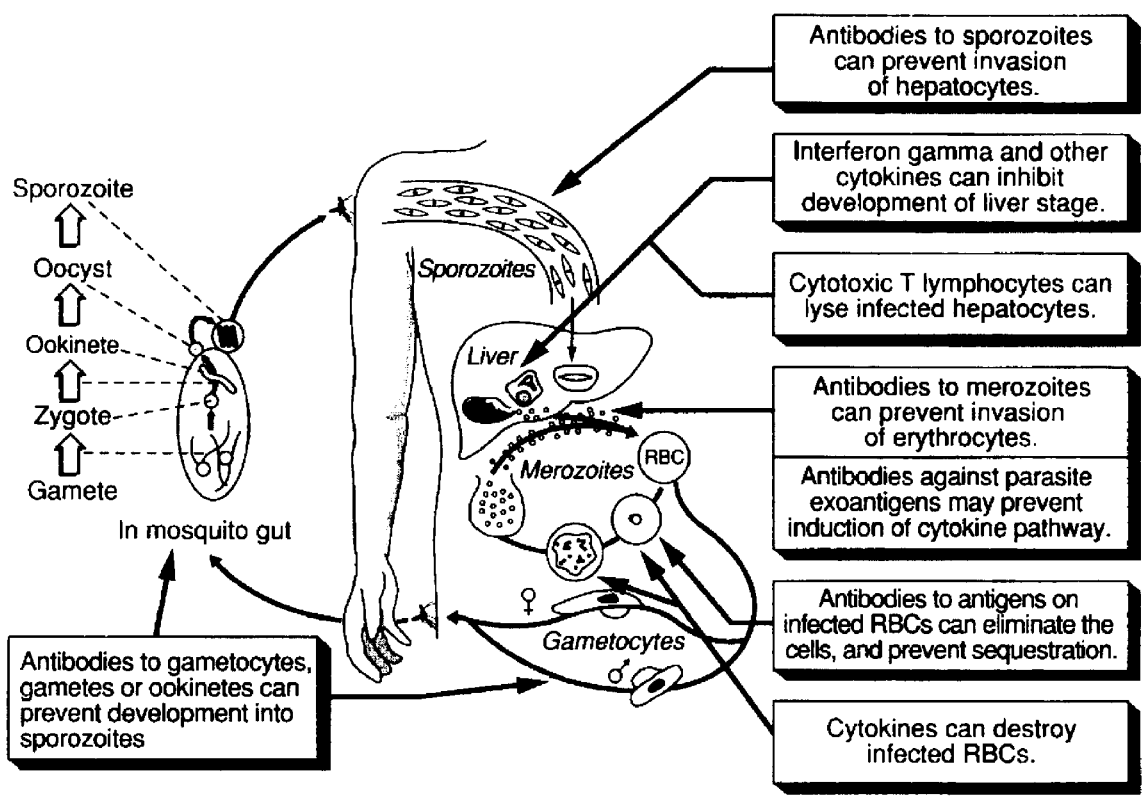
FIG. 1 is a diagram representing the life cycle of the malaria parasite Plasmodium in a mammal.
Figure 5:
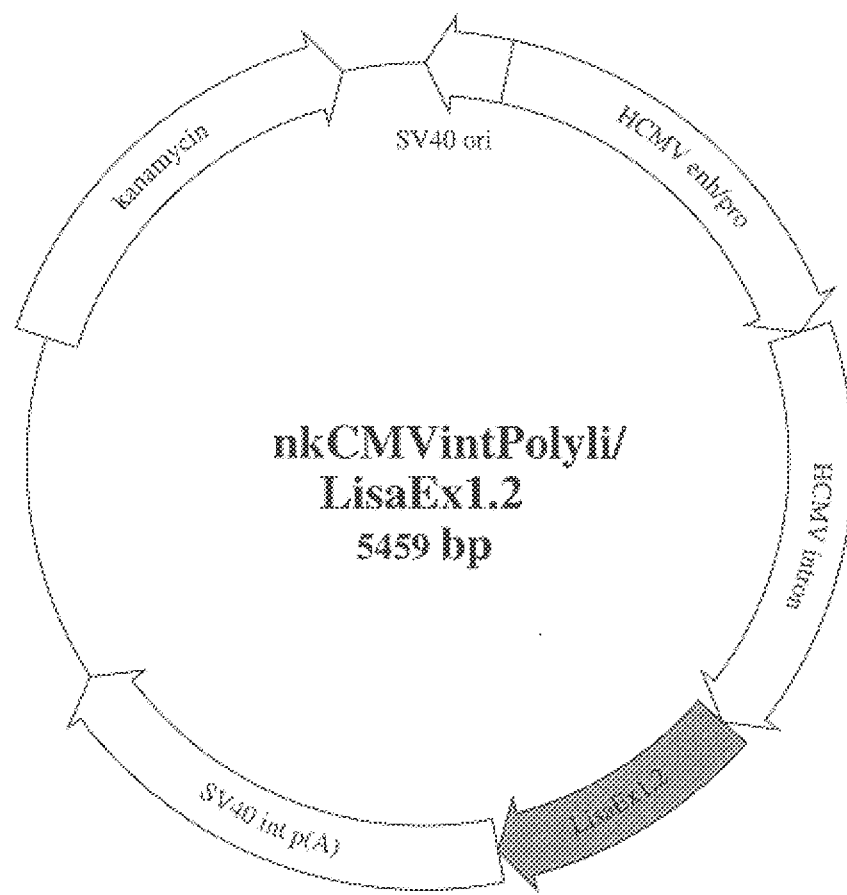
FIG.5 is a schematic diagram of the nkCMVintPolyli/LisaEx1.2 DNA vaccine.

During the development of a uninucleate sporozoite to a mature liver stage schizont with thousands of uninucleate merozoites, there is expression of many as yet uncharacterized parasite antigens that may be the targets of protective immune responses. To identify such antigens, the inventors immunized BALB/c ByJ mice with P. yoelii liver stage parasites and produced monoclonal antibodies (mAbs). A mAb designated Navy Yoelii Liver Stage 3 (NYLS3), that recognizes P. yoelii hepatic and erythrocytic stage parasites, was identified. The inventors have found that this mAb eliminates infected hepatocytes in culture in a species-specific manner, and provides partial protection against sporozoite and blood stage challenge in mice.

Monoclonal antibody NYLS3 recognizes a 17-kDa protein designated P. yoelii Hepatocyte Erythrocyte Protein 17 (PyHEP17,) that is not expressed in sporozoites, but is expressed within 6 hours after sporozoite invasion of hepatocytes. This protein is abundantly expressed in late liver schizonts, and is expressed in infected erythrocytes. NYLS3 also has significant inhibitory activity against infected hepatocytes and infected erythrocytes. It eliminates infected hepatocytes from culture in a species-specific manner. In mice challenged with sporozoites or infected erythrocytes, NYLS3 delays the onset of parasitemia and reduces the level of parasitemia for several days.

The PyHEP17 protein is encoded by a gene comprising at least two exons. The inventors constructed a DNA vaccine consisting of exon 1 (121 base pairs) and 65% of exon 2 (221 base pairs). The vaccine was administered to mice intramuscularly. The mice raised antibodies that recognized both liver-stage and blood-stage P. yoelii parasites. Some mice of each of four strains differing in their MHC class I haplotype that received the vaccine were completely protected against development of blood-stage parasitemia. In some mice which were not protected, the onset of parasitemia was delayed indicating that the vaccine was also having an effect in these mice.

The detailed description that follows provides the preferred embodiments of the invention outlined above, and shows that the invention can be practiced using other species of Plasmodium, including P. falciparum, P. vivax, P. ovale and P. malariae, which infect humans. The DNA vaccine of the invention can also be combined with other DNA vaccines, recombinant proteins or synthetic peptides, or parts thereof, to provide enhanced protection against malaria infection. Also, the recombinant proteins or synthetic peptides of the invention, or parts thereof, can be combined with other DNA vaccines to provide enhanced protection against malaria infection. The plasmid constructs of the DNA vaccine are incorporated in a composition comprising a suitable and acceptable art recognized pharmaceutical reagent that is benign (non-reactive with) to the plasmid construct. The plasmid construct can be utilized by injection (intramuscular, intravenous, intradermal, subcutaneous), inhalation, topical application, or ingestion of the DNA into humans to induce protective immune responses to malaria. The specific doses to be delivered are determined after studies of safety, toxicity, and immunogenicity so as to induce the best immune responses without placing the patient at increased risk and without inducing unacceptable side effects. The methods for identifying appropriate doses are well known in the art. The DNA or cDNA encoding Plasmodium species proteins could be inserted into any vector (circular or linear) so as to induce immune responses against these proteins, or could be injected without insertion into a vector. In an earlier application filed by some of the same inventors, U.S. patent application Ser. No. 08/155,888, filed Nov. 23, 1993, an embodiment is described of a plasmid vector constructed for use in the delivery in vivo of polynucleotides (cDNA, DNA, RNA,) the sequences of which encode the synthesis of molecules that provide beneficial therapeutic or immunological (protective) responses in mammalian subjects. This embodiment is applicable to the invention of this application.

1. Production of NYSL3 Monoclonal Antibody

To produce liver stage parasites, P. yoelii sporozoites were isolated from the salivary glands and thoraces of infected Anopheles stephensi mosquitoes, and injected intravenously into mice; livers were removed from the mice, and liver cell suspensions were prepared. These liver stage parasites were used to immunize mice for the production of mAbs, for the preparation of antigen slides for the indirect fluorescent antibody testing (IFAT), and for the preparation of antigen extract for Western blot analysis.

Infected hepatocytes from P. falciparum and other species of human malaria can be obtained by infecting in vitro human hepatocytes (P. falciparum, P. vivax) or human hepatoma cells (*P. vivax*) with their respective sporozoites. These infected hepatocytes can be used in the production of mAbs against the respective human malaria species.

To produce *P. yoelii* and liver stage monoclonal antibodies, mice were intravenously immunized with liver schizonts produced in vivo. Spleen cells were isolated from the mice and fused with myeloma cells. In one embodiment, the X63.Ag8.653 nonimmunoglobulin secreting mouse myeloma cells using a method described by Danforth et al. were used. However, other myeloma cells including but not limited to Sp2/o, NSO/U, P3-X63-Ag8 can be used. The resulting hybridoma should produce an antibody that recognizes at least one antigen of the injected schizonts. Hybridomas secreting antibodies can be screened by IFAT or other suitable methods, and the positive hybrids are cloned by limiting dilution.

Here, a hybridoma clone secreting a selected mAb (NYLS3) was expanded for the production of ascitic fluids. This mAb, designated Navy *Yoelii* Liver Stage 3 (NYLS3), was purified from ascitic fluids using a Staphylococcus protein A affinity column. However, any suitable purification method can be used.

Recognition of infected hepatocytes and erythrocytes by a monoclonal antibody such as NYLS3 can be assessed by incubating the mAb with air-dried, liver schizonts fixed in cold methanol, and air-dried blood stage parasites. Such methods can also be used to detect recognition of sporozoites by other monoclonal antibodies using air-dried sporozoites.

2. NYLS3 Inhibits Liver Stage Parasite Development In Vitro

The selected monoclonal antibodies can be tested for their in vitro effect on liver stage parasite development. In one embodiment, monoclonal antibodies are tested in the Inhibition of Liver Stage Development Assay (ILSDA) for their inhibitory effects on *P. yoelii* liver stage parasite development.

In a parallel experiment to demonstrate stage-specific inhibition, NYS1, an IgG3 mAb directed against *P. yoelii* sporozoites, was used, and NVS3, an IgG3 mAb directed against *P. vivax* sporozoites, was used as a control. NYLS3 was also tested against liver stages of *P. berghei* to demonstrate species-specific inhibition, and NFS1 was used as a control.

These experiments showed that even when added after sporozoites had invaded hepatocytes, mAb NYLS3 eliminated *P. yoelii*-infected hepatocytes from culture.

To demonstrate the stage specificity of inhibitory activity, the assay was conducted with NYS1, a monoclonal antibody that recognizes the *P. yoelii* CSP, and inhibits sporozoite invasion of hepatocytes in vitro. This monoclonal antibody had greater inhibitory activity than NYLS3 when incubated with sporozoites prior to their invasion, but significantly less activity when added after sporozoites had invaded hepatocytes.

Significantly, NYLS3 clearly demonstrated an inhibitory effect on the infected hepatocytes after sporozoites had invaded. To demonstrate the species-specific inhibitory activity of NYLS3, the ILSDA was conducted with the closely related rodent malaria parasite, *P. berghei*. NYLS3 had no inhibitory activity against *P. berghei*-infected hepatocytes. In addition, NYLS3 does not recognize *P. berghei* or *P. falciparum*-infected hepatocytes.

3. NYLS3 Inhibits Liver Stage Parasite Development In Vivo

The selected monoclonal antibodies can be tested for their effects on malaria infection in vivo. In the case of *P. yoelii*, mice are an appropriate experimental model. For testing strains of malaria that infect humans, suitable animal models include Saimiri monkeys, Aotus monkeys, and chimpanzees.

To assess the effect of NYLS3 on in vivo liver stage parasite development in these experiments, mice were injected i.v. with *P. yoelii* sporozoites. After sporozoite inoculation, each mouse was injected with one of the following: NYLS3 in 0.2 ml PBS; a control mAb (NFS1, IgG1, *P. falciparum* anti-sporozoite mAb) in PBS; or PBS alone. When compared to PBS, NYLS3 reduced the numbers of liver schizonts by 35–45%.

Appropriate mAbs for use as controls when testing mAbs directed against Plasmodium species that infect humans include any isotype-matched mAb that does not recognize the respective antigens of Plasmodium species.

To determine if NYLS3 would protect against challenge in vivo, mice that received NYLS3 in passive transfer were challenged by i.v. inoculation of *P. yoelii* sporozoites or *P. yoelii*-infected erythrocytes. None of the mice that received NYLS3 were completely protected against challenge with either sporozoites or infected erythrocytes. However, when compared with mice that received the control mAb (NFS1, IgG1), the mice that received NYLS3 had a delay in onset of parasitemia, and a reduction in the level of parasitemia within the first five days after challenge with either sporozoites or infected erythrocytes. By day 6 there was no difference in the level of parasitemia among these groups of mice.

To assess the effect of NYLS3 on in vivo blood stage infection, mice received i.v. injections of NYLS3, a control mAb (NFS1), or PBS, and were challenged by administration of sporozoites or infected erythrocytes. Six groups of mice were used in this study. Groups 1–3 received 4 injections of NYLS3 or control mAb NFS1 at 1, 36, 72, and 108 hours after i.v. inoculation with *P. yoelii* sporozoites. Groups 4–6 received an i.v. injection of *P. yoelii*-infected erythrocytes after the first dose of NYLS3, NFS1 or PBS, and 3 additional doses after the first dose. Parasitemias were determined daily through day 21 beginning on day 3 after sporozoite challenge and day 1 after blood stage challenge.

4. Characteristics of the PyHEP17 Gene

The methods described above are used to identify and test a monoclonal antibody that recognizes an antigen expressed by malaria schizonts in infected mammals during the liver stage. The antigen is also expressed by infected erythrocytes. The gene encoding the antigen of interest can be identified using methods described below.

First, DNA or cDNA is obtained from the relevant malaria parasite. The DNA can be obtained from erythrocytes infected with the parasite. The DNA or cDNA may also be obtained from sporozoites isolated from the salivary glands and thoraces of infected mosquitoes, or from infected hepatocytes.

A genomic expression library is constructed using bacterial host cells transformed with a DNA library representative of the malaria parasite genome. Examples of useful host cells include *E. coli*. The transformed host cells are screened to identify clones expressing the antigen of interest. The cells can be screened (immunoscreening) using the monoclonal antibody which recognize the antigen of interest. Alternatively, probe screening, with DNA fragments or specific oligonucleotides, can be carried out to identify a clone containing the antigen of interest. Once a clone is identified, the mRNA is obtained from the cells. The mRNA is reverse transcribed to produce first strand cDNA, which can be amplified using polymerase chain reaction. In the present experiments, primers for the amplification were based on predicted sequence from the Lisa3 clone DNA sequence.

The amplified DNA fragment is then digested with restriction enzymes and cloned into an appropriate like-digested plasmid. A clone containing the whole or partial gene encoding the antigen of interest is identified by further screening with the appropriate monoclonal antibody, DNA fragment or specific oligonucleotides. The DNA fragment can then be isolated and sequenced for further study.

In these experiments, P. yoelii 17X (NL) parasite DNA was prepared from BALB/c mouse parasitized erythrocytes. A P. yoelii λ 11 genomic expression library was constructed and screened for antigen-expressing clones using monoclonal antibody NYLS3. The derived genomic DNA sequence of the plasmodial DNA from immunoreactive clones was determined. Reverse transcription-polymerase chain reaction amplification of cDNA from blood stage parasite mRNA was performed with the following amplifiers (Lisa1 and Lisa Ex2) using oligo-dT primed 1st strand cDNA as the template: Lisa1, 5'-GGA ATT CAT GAA AAT CAA TATA AGC T-3' Seq. I.D. No 7; Lisa Ex2, 5'-GGG ATC CTG ATT TGC CAA TTT GAA A-3' Seq. I.D. No 8. The process can also use (2) random hexamer primed first strand DNA, or (3) specific oligonucleotide primed first strand cDNA as the template. The amplified DNA fragment was digested with EcoRI and BamHI, then cloned into like-digested plasmid pUC18 to obtain pUC18/LisaEx1.2. The cDNA sequence was derived from the cloned PCR fragment in pUC18/LisaEx1.2 by DNA sequence determination from alkaline-denatured double-stranded templates. Similar procedures can be used to obtain cDNA corresponding to additional exons within the gene, or homologs thereof.

Figure 6:
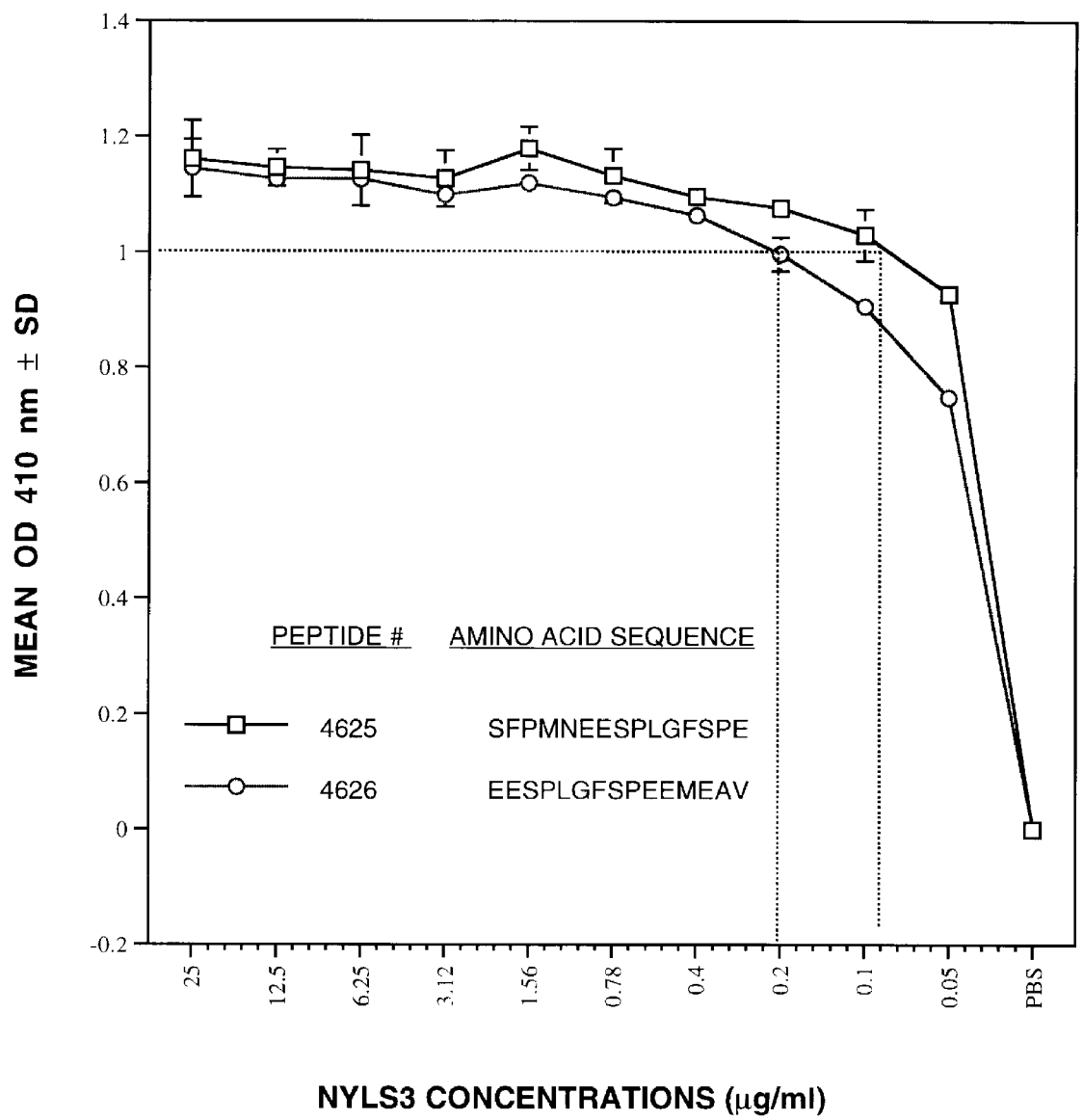
FIG. 6 is a graph showing the reactivity of NYLS3 monoclonal antibody against P. yoelii liver stage peptides #4625 (SEQ ID NO: 1) and #4626 (SEQ ID NO: 2).

An immunoreactive λ 11 clone designated Lisa3 was selected based on its recognition by the monoclonal anti-PyHEP17 antibody NYLS3. The DNA sequence and the possible open reading frames encoding deduced peptide sequences for this orientation of the plasmodial DNA of the Lisa3 clone were analyzed and are shown in Seq. ID #5. The relatedness between the protein PyHEP17 and the peptide encoded by the Lisa3 clone was demonstrated immunologically with overlapping synthetic peptides and the monoclonal antibody NYLS3. Both synthetic peptides SFPMNEESPLGFSPE Seq I.D. No 1 and EESPLGFSPEEMEAV Seq. I.D. No 7 (FIG. 6; Seq ID #5, second reading frame between bases 1028–1105) were immunoreactive with NYLS3 as determined by ELISA. This demonstrates that the epitope of this antibody is within the peptide sequence SFPMNEESPLGFSPEEMEAV OVERLAP of Seq. I.D. Nos 1 & 2 and suggests that it is included in the sequence EESPLGFSPE Seq. I.D. No 9. These results show that the Lisa3 clone contains at least part of the PyHEP17 gene.

Striking amino acid sequence identity was found between one of these opening reading frames of the PyHEP17 gene sequence (Seq. ID #5 692–1111) and a region of the amino acid sequence of the Exp1 antigen from the human malaria parasite, P. falciparum (Hope et al. [PfExp1 (ID PFAG51ER)]: between bases 776–994, a 73 amino acid stretch displayed 59% amino acid sequence identity with the corresponding region of PfExp1. This region was localized to exon 2 of PfExp1 [(ID PFEXP1G)] (Simmons et al.).

This discovery is the first suggestion that PyHEP17 is the P. yoelii homologue of PfExp1. No other strikingly homologous regions were observed, but an open reading frame of similar size to exon 1 of PfExp1 and distance from the putative exon 2 of the sequence of the clone Lisa3 was detected, and it contained an ATG codon at base 378 (Seq. ID #5, 327–509).

The gene encoding PyHEP17 has been deposited with the American Type Culture Collection, Rockville, Md., U.S.A. on 7 Oct. 1994, Accession Number ATCC 75,918.

To determine whether these were indeed exons, a cDNA clone, designated pUC18/LisaEx1.2, was isolated from blood stage parasite mRNA via RT-PCR. The oligonucleotide primers for the amplification were predicted from the Lisa3 sequence to amplify a cDNA that would include all of the putative exon 1 beginning with the initiation ATG and that portion of putative exon 2 homologous to PfExp1. The cDNA sequence of the insert from clone pUC18/LisaEx1.2 and the derived amino acid of this cDNA is shown in FIG. 8. The alignment shown in FIG. 7 demonstrated 47% deduced amino acid homology of this not yet full-length cDNA with that of the overlapping region of PfExp1, which is clearly indicative of relatedness. Furthermore, an anti-EXP1 mAb recognizes COS cells transfected with the LisaEx1.2 DNA vaccine. This vaccine does not contain the NYLS3 epitope. Together, the sequence identity and immunological data indicate that PyHEP17 is the P. yoelii homologue of PfExp1.

The methods described above can be used to identify and isolate homologous genes from P. vivax, P. ovale, and P. malariae, in addition to the P. falciparum homologue which has been identified. The protein characteristics, monoclonal antibody, cDNA and DNA sequence disclosed herein can be used to detect proteins homologous to PyHEP17 in other human malaria species including P. vivax, P. malariae, and P. ovale. For example, oligonucleotide probes based on the DNA sequence or cloned fragments of the PyHEP17 gene may be used by standard techniques to screen genomic libraries constructed from human malaria species. The oligonucleotide probe will have a length adequate for stable hybridization, and will normally be about 15 nucleotides in length. Such probes can be fragments of nucleic acids having the nucleotide sequence of Seq. ID #5 or FIG. 8 or other sequences included in the PyHEP17 gene (e.g. exon 3 or other exons). The cloned gene encoding PyHEP17 may be expressed in a variety of prokaryotic and eukaryotic expression systems. Crude or purified recombinantly expressed PyHEP17 can be used to produce additional polyclonal or monoclonal antibodies or specific immune T lymphocytes, which can be used to screen genomic expression or cDNA libraries in order to identify PyHEP17 homologs in human malaria species.

5. Construction of nkCMVintPolyli/LisaEx1.2 DNA Vaccine and Immunization with nkCMVintPolyli/LisaEx1.2 DNA Vaccine Traditional vaccines contain one or more antigens of a bacteria or virus, wherein the antigens are capable of stimulating an immune response against the bacteria or virus. More recent techniques allow inoculation of mammals using DNA encoding the antigen. Such methods are described by Wang et al. and by Jiao et al. The inventors have successfully vaccinated mice of 4 strains differing in their class I MHC haplotype using a DNA vaccine containing exons of the DNA encoding the PyHEP17 antigen. These experiments, and their applicability to vaccination of humans against human malaria species, are discussed in detail below.

In these experiments, a DNA vaccine consisting of exon 1 (121 bp) and 65% of exon 2 (221 bp) of PyHEP17, cloned into a nkCMVintPolyli vector, was constructed. This construct does not include the region of the PyHEP17 protein recognized by NYLS3. The expression of this vector is driven by a Cytomegalovirus promoter.

The pUC18/LisaEx1.2 cDNA clone was digested with HindIII and ECoR1 restriction enzymes to release the cDNA fragment. This cDNA was directionally ligated into like-digested pBluescript SK+. This plasmid was digested with PstI to release the cDNA fragment which was then ligated into the like-digested nkCMVintPolyli vector.

Large-scale quantities of the sequenced nkCMVintPolyli/ LisaEx1.2 plasmid and a control plasmid nkCMVintPolyli were prepared by the alkaline lysis method and purified by banding and rebanding on cesium chloride gradients. DNA was resuspended at a final concentration of 2 mg/ml in sterile saline.

To test the nkCMVintPolyli/LisaEx1.2 DNA construct as a vaccine, mice of each of the strains BALB/c ($H-2^d$), C57BL/6 ($H-2^b$), B10.BR ($H-2^k$), B10.Q ($H-2^q$), and A/J ($H-2^a$) were immunized intramuscularly in each tibialis anterior muscle with three doses of 200 $\mu$g/100 $\mu$l nkCMVintPolyli/LisaEx1.2 DNA vaccine per mouse at three week intervals. The vector is not limited to nkCMVintPolyli. Any suitable vector can be used to construct the DNA vaccine. Mice of each of the strains were also immunized with the control plasmid nkCMVintPolyli. Serum was collected from all mice between each immunization, and was tested for recognition of air-dried liver-stage and blood-stage *P. yoelii* parasites by the indirect fluorescent antibody test (IFAT). Two weeks after the third immunization, mice were challenged with 100 infectious *P. yoelii* sporozoites (>50 $ID_{50}$). Blood smears were collected from day 4 to day 14 following challenge, stained with Giemsa, and the development of blood-stage parasitemia monitored. Protection was defined as the complete absence of blood stage parasitemia.

Antibodies induced by the nkCMVintPolyli/LisaEx1.2 DNA vaccine recognized both liver-stage and blood-stage *P. yoelii* parasites, as demonstrated by IFAT. Both liver-stage specific and blood-stage-specific antibody titres were low and not all mice developed blood-stage antibody titres, even after 3 immunizations. Some sera which recognized *P. yoelii* liver-stage parasites did not recognize *P. yoelii* blood-stage parasites, and some sera which recognized *P. yoelii* blood-stage parasites showed little recognition of *P. yoelii* liver-stage parasites. These data indicate that there may be two distinct B cell epitopes present on the region of the gene encoding exon 1 and 65% of exon 2 of the HEP17 protein. One epitope is preferentially recognized by antibodies against liver-stage parasites, and another is preferentially recognized by antibodies against blood-stage parasites. Sera from mice immunized with the control plasmid nkCMVintPolyli did not recognize either liver-stage or blood-stage *P. yoelii* parasites.

Following challenge, 86% of the A/J mice, 33%–43% of the B10.BR mice, 17%–29% of the BALB/c mice and 14%–20% of the B10.Q mice were completely protected against development of blood-stage parasitemia. In some mice which were not protected, the onset of parasitemia was delayed for 4–6 and 4 days in 14–17% of BALB/c and 17% of B10.BR mice, respectively, indicating that the vaccine was also having an effect in these mice.

There was no apparent correlation between liver-stage nor blood-stage antibody titres and protection. Indeed, some mice which were protected did not have detectable antibodies against blood-stage parasites. Data indicated that T cell-mediated immune responses specific for PyHEP17 may play a role in the DNA vaccine-induced protection.

Thus, the inventors have now demonstrated that the antigen PyHEP17, present in both the liver and blood stages of *P. yoelii*, is a target of protective immune responses.

Using the methods described here, DNA can be isolated from any malaria species in which an antigen target for protective antibodies has been identified. Using the DNA, vaccines can be constructed and tested. In the experiments described here, a DNA vaccine against the malaria species *P. yoelii* was tested in mice. Vaccines derived from DNA of human malaria species can also be tested in animal models prior to clinical trials. One of ordinary skill in the art will be familiar with appropriate animal models. For example, vaccines containing antigenic protein from *P. vivax* CSP have been tested in Saimiri monkeys (Collins et al. 1989 and Charoenvit et al. 1991b). Other appropriate animal models for testing DNA vaccines include Aotus monkeys and chimpanzees.

The inventors have found that immunization with a nkCMVintPolyli/LisaEx1.2 DNA vaccine can confer protection against *P. yoelii* sporozoite challenge. Since a monovalent DNA vaccine may not provide complete protection against malaria, the inventors wanted to assess whether immunization with a combination of DNA vaccines encoding different protective antigens could confer complete, and/or additive, protection against malaria.

The DNA vaccines of the invention, which encompass vaccines for protecting humans against malaria, can also be combined with one or more other DNA vaccines to create a combination vaccine. Use of a multi-antigen human sporozoite antigen has been suggested based upon results of tests in mice (Khusmith et al.). One such DNA vaccine has already contained the DNA of the invention and DNA encoding the *P. yoelii* CSP.

Mice were immunized intramuscularly with 100 $\mu$g/mouse of the nkCMVintPolyli/LisaEx1.2 DNA vaccine plus 40 $\mu$g/mouse of a nkCMVintPolyli/CSP DNA vaccine. These vaccines were administered together at the same time in the same sites. Five strains of mice differing in their class I MHC haplotypes were immunized, using the same regime described previously for the nkCMVintPolyli/LisaEx1.2 DNA vaccine (i.e 3 immunizations intramuscularly at 3 week intervals). Mice were challenged with 100 infectious *P. yoelii* sporozoites two weeks after the third immunization.

This combination of the nkCMVintPolyli/LisaEx1.2 DNA vaccine plus the nkCMVintPolyli/CSP DNA vaccine was able to confer complete protection against *P. yoelii* sporozoite challenge in one mouse strain and additive protection in two strains. 100% of BALB/c mice immunized with the combination of DNA vaccines were protected. Only 86% of BALB/c mice immunized with the CSP vaccine and 29% of BALB/c mice immunized with the LisaEx1.2 vaccine were protected. Furthermore, 71% of B10.BR immunized with the combination of DNA vaccines were protected. Only 20% of B10.BR mice immunized with the CSP vaccine and 43% of B10.BR mice immunized with the LisaEx1.2 vaccine were protected. This data indicate that the protection conferred by this combination of DNA vaccines is additive.

Although no C57 BL/6 mice and few B10.Q mice were protected, a delay in the onset of parasitemia was nevertheless observed in some mice which were not protected. A delay of 2–3 days was noted in 29% of the C57 BL/6 mice and of 6 days in 14% of the B10.Q mice, indicating that even in those mice which were not protected, the combined DNA vaccines were having an effect.

Nucleotides encoding any Plasmodium species proteins capable of inducing protection against malaria usable in this invention as DNA vaccines or combinations of DNA vaccines include but are not limited to the known *P. falciparum, P. vivax, P. malariae,* and *P. ovale* CSP; SSP2(TRAP); Pfs16 (Sheba); LSA-1; LSA-2; LSA-3; STARP; MSA-1 (MSP-1, PMMSA, PSA, p185, p190); MSA-2 (MSP-2, Gymmsa, gp56, 38–45 kDa antigen); RESA (Pf155); EBA-175; AMA-1 (Pf83); SERA (p113, p126, SERP, Pf140); RAP-1; RAP-2; RhopH3; PfHRP-II; Pf55; Pf35; GBP (96-R); ABRA (p101); Exp-1 (CRA, Ag5.1); Aldolase; Duffy binding protein of *P. vivax*; Reticulocyte binding proteins; HSP70-1 (p75); Pfg25; Pfg28; Pfg48/45; and Pfg230.

6. Use of PyHEP17 and its Homologs as Vaccines

The methods described herein can be used to produce monoclonal antibodies that recognize antigens expressed during the liver stage and blood stage of malaria infection. Using standard techniques, the antigenic proteins can be isolated and sequenced. Alternatively, as described herein, the DNA encoding the antigenic protein can be cloned and sequenced, thereby providing information from which to deduce the amino acid sequence of the encoded protein.

According to the invention, the protein PyHEP17 is recognized by the monoclonal antibody NYSL3. PyHEP17, expressed by *P. yoelii* during the liver and blood stage of infection, is therefore suitable for testing as a vaccine against malaria infection in mice. In one embodiment, the gene encoding the protein can be used to transfect cells, and the cells are injected into the mice, where they express the antigenic protein. Such methods are described in U.S. Pat. No. 5,198,535, which is incorporated by reference herein.

Given the DNA sequence of the human malaria homologs of PyHEP17, readily obtainable with the present art, it is possible to design a large number of vaccine formulations including but not limited to (1) synthetic peptide vaccines based on the inferred amino acid sequence; (2) recombinant proteins consisting of all or part of the PyHEP17 homolog protein expressed in any of a large number of protein expression systems including but not limited to phage lysogens, bacterial plasmids, yeast plasmids, mammalian cell expression plasmids and viruses, and insect viruses (e.g. baculovirus).

The DNA vaccine of the invention may be given and followed by one or more booster immunizations of one or more components of, or synthetic peptides derived from, the proteins described above. The booster immunization can be given at an interval of 1–4 weeks after the initial administration of DNA vaccine, and can be repeated from about 1 to about 4 times. Usually, 0.5–100 protein $\mu$g/mouse is used for each booster immunization.

Alternatively, the initial immunization could be with one or more components of, or synthetic peptides derived from, the proteins described above. The booster immunization can then be performed using the DNA vaccine, or fragments thereof, or one or more components of, or synthetic peptides derived from the proteins described above.

The booster immunization can also be performed using DNA fragments from the DNA administered as the vaccine, and or a DNA fragment from an exon of the gene, wherein the gene is different from the exons comprising the DNA vaccine.

The vaccine and/or booster immunization polypeptides of the invention can be comprised of one or more polypeptides encoded by the DNA of the invention. Those polypeptides, or immunogenic fragments thereof, can be synthetic or produced by recombinant technology. Such polypeptides include those shown in FIGS. 6, 8 and 9, and fragments thereof.

Vaccines produced by these methods may be administered to humans in any pharmacologically active form and dosage with any pharmacologically appropriate adjuvant including but not limited to saline, aluminum hydroxide, and liposomes. In any of the above vaccines, components derived from any Plasmodium species proteins capable of inducing protection against malaria including but not limited to the known *P. falciparum, P. vivax, P. malariae,* and *P. ovale* CSP; SSP2(TRAP); Pfs16 (Sheba); LSA-1; LSA-2; LSA-3; STARP; MSA-1 (MSP-1, PMMSA, PSA, p185, p190); MSA-2 (MSP-2, Gymmsa, gp56, 38–45 kDa antigen); RESA (Pf155); EBA-175; AMA-1 (Pf83); SERA (p113, p126, SERP, Pf140); RAP-1; RAP-2; RhopH3; PfHRP-II; Pf55; Pf35; GBP (96-R); ABRA (p101); Exp-1 (CRA, Ag5.1); Aldolase; Duffy binding protein of *P. vivax*; Reticulocyte binding proteins; HSP70-1 (p75); Pfg25; Pfg28; Pfg48/45; and Pfg230, can be used.

In mice, the DNA vaccine is administered in an amount of about 0.1 $\mu$g–500 $\mu$g DNA/mouse, preferably 1–100 $\mu$g, and most preferably 1–50 $\mu$g. The DNA vaccine can be administered to a mammal intradermally, intramuscularly, intranasally or any other suitable method, including a gene gun, with or without pretreatment of the target tissue.

Although it is not necessary for practicing this invention, a Universal Helper T Cell Epitope, such as $P_2P_{30}$ derived from tetanus toxin, may be used to enhance the host immune response to the vaccines. The $P_2$ epitope can have the amino acid sequence QYIKANSKFIGITEL Seq. I.D. No 10 or the translated nucleotide sequence. The $P_{30}$ epitope can have the amino acid sequence FNNFTVSFWLRVKVSASHLE Seq I.D. No 11 or the translated nucleotide sequence (Valmori, D. et al., *J. Immunol.* 149:717–721, 1992). In DNA vaccines, DNA encoding the epitopes $P_2P_{30}$ can be co-expressed with the DNA encoding the target antigen.

EXAMPLES

Example 1

Preparation of liver stage parasites

Materials and Methods

Animals—Female, 6–10 week old, BALB/c ByJ mice (The Jackson Laboratory, Bar Harbor, Me.) were used.

Parasites—The 17XNL (nonlethal) strain of *P. yoelii* was used in all studies.

To produce liver stage parasites, *P. yoelii* sporozoites were isolated from the salivary glands and thoraces of infected *Anopheles stephensi* mosquitoes (Pacheco et al.). An aliquot of 0.2 ml of a suspension containing $2-5\times10^6$ sporozoites suspended in Medium 199 (Gibco BRL, Gaithersburg, Md.) supplemented with 5% normal mouse serum was injected i.v. into the tail vein of each mouse. Forty-four hours later, livers were removed from the mice, and liver cell suspensions were prepared in the same medium.

The number of liver schizonts was counted by microscopic examination of Giemsa-stained liver cell suspensions that were air-dried on multi-spot antigen slides. These liver stage parasites were used to immunize mice for the production of mAbs, for the preparation of antigen slides for the indirect fluorescent antibody testing (IFAT), and for the preparation of antigen extract for Western blot analysis.

To produce in vitro liver stages, $10^5$ mouse hepatocytes suspended in 0.3 ml of MEM (Quality Biological Inc., Gaithersburg, Md.) containing 10% FBS was added into each well of an eight-chamber Lab-Tek culture slide (Nunc, Inc., Naperville, Ill.) and incubated for 24 hours at 37° C. in an atmosphere of 5% $CO_2$, 95% air. The medium was removed, $6\times10^4$ sporozoites suspended in 50 $\mu$l of culture medium was added to the culture, and further incubated for 3 hours. The cultures were washed several times to remove unattached sporozoites, then incubated in fresh medium for 6, 24, 48 and 72 hours. These in vitro liver stage parasites were evaluated by IFAT and immunoelectron microscopy, and were used as targets in the assay to determine inhibitory effect of mAbs on liver stage parasite development.

Production of Monoclonal Antibodies (mAbs)

Mice were intravenously immunized three times at 2 week intervals with $1-8\times10^3$, 44 h-liver schizonts produced in vivo. These mice did not develop any detectable blood stage infection during the course of immunization as determined by Giemsa staining of their blood films. Three days after the last immunization, spleen cells were isolated from the mice and fused with the X63.Ag8.653, nonimmunoglobulin secreting mouse myeloma cells (Danforth et al.).

Hybridomas secreting antibodies were screened by IFAT (Charoenvit et al. 1987) using air-dried, 44 hours in vivo liver schizonts or cryosections of liver schizonts as antigens. The positive hybrids were cloned by limiting dilution. A hybridoma clone secreting a selected mAb (NYLS3) was expanded for the production of ascitic fluids. This mAb was purified from ascitic fluids using a Staphylococcus protein A affinity column (Ey et al.).

Indirect fluorescent antibody test (IFAT)

Recognition of sporozoites and infected hepatocytes and erythrocytes by NYLS3 was assessed by incubating NYLS3 for 30 min at 37° C. with air-dried sporozoites; 6, 24, 48 and 72 hours in vitro liver schizonts that were fixed for 10 min in cold methanol; and air-dried blood stage parasites. The slides were washed three times with PBS and further incubated for 30 min with FITC-labeled goat anti-mouse IgG (Kirkegaard & Perry Laboratories Inc., Gaithersburg, Md.). The slides were washed three times with PBS, mounted in 30% glycerol in PBS, and examined under an Olympus UV microscope.

Immunoelectron microscopy

Sporozoites, 72 hours in vitro-produced liver schizonts, and blood stage parasites obtained from infected mice were examined by immunoelectron microscopy using NYLS3 mAb as the detecting antibody. Parasites were fixed for 20 min at 4° C. in 1% paraformaldehyde, 0.2% glutaraldehyde in 0.1M phosphate buffer pH 7.4. Fixed specimens were washed in 0.1M phosphate buffer, pH 7.4, and dehydrated in ascending concentrations of ethanol and subsequently embedded in LR gold resin (Polyscience Inc., Warrington, Pa.) containing 0.75% benzoin methyl ether as an ultraviolet initiator (Atkinson et al.). Ultrathin sections were incubated for 15 min in PBS containing 5% nonfat dry milk and 0.01% Tween-20, and then incubated for 18 hours at 4° C. with undiluted supernatant NYLS3 mAb (approximate concentration 2–10 µg antibody/ml).

After washing with PBS containing 1% BSA and 0.1% Tween-20 (PBT), the grids were incubated for 1 hour at room temperature with a 1:20 dilution of 15 nm gold-labeled goat anti-mouse IgG (Fc) (Amersham International Inc., UK), rinsed with PBT, and fixed for 15 min in 2.5% glutaraldehyde in 0.1M phosphate buffer, pH 7.4, to stabilize the gold. The grids were rinsed with distilled water, air-dried, and stained with 2% uranyl acetate and lead citrate. Samples were examined in a JEOL 100CX electron microscope. To test the specificity of the method, control sections of liver stage parasites were incubated with unrelated mAb and gold probes or gold probes alone.

Western blot analysis

P. yoelii sporozoites, infected erythrocytes, and infected hepatocytes were extracted for 1 hour at room temperature in PBS containing 1% SDS, in the presence of protease inhibitors (0.34 mg/ml of PMSF, 25 µg/ml of antipain, and 25 µg/ml of leupeptin). The soluble antigens were collected after centrifugation at 15,000×g for 10 min. The parasite antigens were separated from the sporozoite, blood stage and liver stage extracts by SDS/PAGE using a 12% polyacrylamide gel (Laemmli et al.). Proteins were electrophoretically transferred from the gels onto sheets of nitrocellulose at 70 V in a Bio Rad Trans-blot Cell (Towbin et al.). The sheets were blocked overnight at 4° C. in PBS containing 3% nonfat dry milk and 0.05% Tween-20, washed three times in a washing buffer (PBS containing 0.05% Tween-20) and cut into small strips.

The strips were incubated for 2 hours with a 1:10 dilution of NYLS3 culture supernatant, washed three times in a washing buffer, and incubated for 2 hours with a 1:1000 dilution of HRP-labeled goat anti-mouse IgG (Kirkegaard & Perry Laboratories Inc., Gaithersburg, Md.). The strips were washed again before adding a substrate solution (30 mg of 4-chloro-1-naphthol in 10 ml of cold methyl alcohol plus 30 µl of 3% $H_2O_2$ in 50 ml of PBS). Color reaction was allowed to develop for a maximum of 45 min. All reaction steps except blocking were performed at room temperature.

Inhibition of liver stage development assay (ILSDA)

Monoclonal antibodies were tested in the ILSDA for their inhibitory effects on P. yoelii liver stage parasite development as previously described (Mellouk et al.). Briefly, mouse hepatocytes were seeded in MEM (Quality Biological, Inc., Gaithersburg, Md.) containing 10% FBS, in eight-chamber LabTek plastic slides (Nunc, Inc., Naperville, Ill.) at $1 \times 10^5$ cells/chamber. After incubation for 24 hours at 37° C. in an atmosphere of 5% $CO_2$, 95% air, the medium was removed and 100 µg/ml NYLS3 and $6 \times 10^4$ sporozoites suspended in culture medium were either simultaneously added to hepatocyte cultures, or the antibody was added at 3 or 24 hours after sporozoite inoculation.

The cultures were incubated for varying periods: 0–3 h, 3–24 h, and 24–48 hours. At the end of the incubation period, NYLS3 was removed by washing with the medium, and the cultures were further incubated in antibody free-medium for a total of 48 hours. The cultures were then fixed for 10 min in cold methanol, stained by NYLS3 supernate mAb and FITC-labeled goat anti-mouse IgG. Two negative control mAbs were used in this study: Tryp., an IgG1 mAb directed against Trypanosoma rhodesiense (a gift from Dr. Ted Hall, Walter Reed Army Institute of Research), and NFS1, an IgG1 mAb specific for P. falciparum sporozoites.

In a parallel experiment to demonstrate stage-specific inhibition, NYS1, an IgG3 mAb directed against P. yoelii sporozoites (Charoenvit et al., 1987, 1991a) was used, and NVS3, an IgG3 mAb directed against P. vivax sporozoites (Charoenvit et al., 1991b) was used as a control. NYLS3 was also tested against liver stages of P. berghei to demonstrate species-specific inhibition and NFS1 was used as a control. The number of liver schizonts in each culture was counted using an Olympus UV microscope and the mean number of liver schizonts in triplicate cultures was recorded. Percent inhibition was calculated based on the numbers of schizonts in cultures to which the control mAb had been added.

Passive immunization

To assess the effect of NYLS3 on in vivo liver stage parasite development, three groups of 3–4 mice were injected i.v. with $5 \times 10^5$ P. yoelii sporozoites. At 3 and 24 hours after sporozoite inoculation, 2.5 mg NYLS3 in 0.2 ml PBS, a control mAb (NFS1, IgG1, P. falciparum anti-sporozoite mAb) in PBS, or PBS alone was injected into the tail vein of each mouse. At 43 hours after sporozoite inoculation, liver was removed from each mouse and a hepatocyte cell suspension was prepared in Medium 199 (Gibco BRL, Gaithersburg, Md.) without serum, and adjusted to a final concentration of $2.5 \times 10^7$ hepatocytes/ml.

An aliquot of 10 µl of liver cell suspension containing $2.5 \times 10^5$ hepatocytes was dispensed into 10 wells of a multi-spot antigen slide ($2.5 \times 10^4$ hepatocytes/1 µl/well). The slides were air-dried, stained by NYLS3 and FITC-labeled goat anti-mouse IgG, and examined under an Olympus UV microscope. The number of liver schizonts was counted on 2–4 slides from each mouse. For each treatment group, the mean number of liver stage parasites/$2.5 \times 10^5$ hepatocytes was recorded. Statistical analysis of the level of liver stage infection between experimental and control groups was determined using the Wilcoxon ranked sum test.

To assess the effect of NYLS3 on in vivo blood stage infection, mice received i.v. injections of NYLS3, a control mAb (NFS1), or PBS and were challenged by administration of sporozoites or infected erythrocytes. Six groups of 10 mice were used in this study. Groups 1–3 received 4 injections of 2.5 mg NYLS3 or control mAb NFS1 in 0.2 ml PBS, or 0.2 ml PBS at 1, 36, 72, and 108 hours after i.v. inoculation with 100 P. yoelii sporozoites. Groups 4–6 received an i. v. injection of 200 P. yoelii infected erythrocytes 1 hours after the first dose of NYLS3, NFS1 or PBS, and 3 additional doses at 36, 72, and 108 hours after the first dose.

Parasitemias were determined daily through day 21 by Giemsa stained thin blood films beginning on day 3 after sporozoite challenge and day 1 after blood stage challenge. A total of 200 grid-fields (average of 165 erythrocytes/field) were examined from a slide obtained from each mouse, and the frequency of infection and percent parasitemia were calculated. Frequency of infection between groups was compared using Fisher's exact test. Differences between group mean parasitemias with 95% confidence limits were evaluated using a signed rank test.

Results

Production of mAbs

A total of 12 hybridoma lines secreting antibodies against P. yoelii liver stages were produced in one fusion experiment. All lines produced IgG1 antibodies as determined by gel double diffusion. All produced the same pattern of indirect fluorescent antibody test (IFAT) reactivity on 44 hours in vivo liver schizonts. The hybridoma lines were cloned and a total of 24 hybridoma clones were obtained. All clones produced IgG1 antibodies with the same pattern of IFAT reactivity when tested against in vivo liver schizonts. NYLS3 produced the strongest reactivity by IFAT, and was therefore selected for further characterization.

Stage specific parasite recognition by NYLS3

NYLS3 does not react with P. yoelii sporozoites by IFAT, but reacts strongly with cryo-sections of 44 hours in vivo liver schizonts. The IFAT reactivity is present at the periphery of the parasites (FIG. 2A). This mAb is species-specific, it does not react with P. berghei or P. falciparum liver schizonts produced in primary cultures of mouse or human hepatocytes respectively, or liver schizonts from a chimpanzee infected with P. falciparum sporozoites (not shown). NYLS3 reacts with hepatocyte cultures infected with irradiated sporozoites (FIG. 2B) and non-irradiated sporozoites (FIG. 2C–FIG. 2F). The protein recognized by NYLS3 can be detected 6 hours after sporozoite invasion, and is detectable throughout the liver stage cycle with increasing expression as the parasite matures (FIG. 2C–FIG. 2F). This protein is also expressed throughout the erythrocytic cycle and on free merozoites (FIG. 2G–FIG. 2I).

Western blot analysis

NYLS3 reacts with a 17-kDa protein band from an extract of P. yoelii blood stage parasites (FIG. 3, lane 1). The protein is designated P. yoelii hepatic and erythrocytic stage protein, 17-kDa or PyHEP17. This mAb does not react with an extract of normal mouse erythrocytes (FIG. 3, lane 2), or an extract of P. yoelii sporozoites (FIG. 3, lane 3). Although the mAb reacts strongly with liver stages by IFAT, we were unable to demonstrate protein by immunoblot analysis using an extract prepared from liver schizonts obtained from the infected mice or from the in vitro infected mouse hepatocytes. This inability to identify parasite proteins by immunoblot of infected hepatocytes is completely consistent with our previous experience (unpublished), and is probably a reflection of the low ratio of infected to uninfected hepatocytes in any preparation; 40–400 infected hepatocytes in 100,000 uninfected hepatocytes.

Immunoelectron microscopic localization of PyHEP17 protein

Although NYLS3 reacts with liver and blood stage parasites (FIGS. 4A and B), it does not react with sporozoites in immunoelectron microscopy (not shown). The protein recognized by NYLS3 is present on the parasitophorous vacuole membrane (PVM) surrounding liver schizonts in mouse hepatocytes cultured for 72 hours after sporozoite inoculation, as shown by gold particle deposition on the PVM (FIG. 4A). However, gold particles were not detectable on the surface of infected hepatocytes (SH). The protein is also present on the PVM and cleft (C) of infected erythrocytes (trophozoites) (FIG. 4B), and on the membranes of blood stage merozoites (not shown).

Inhibition of liver stage development assay (ILSDA)

Even when added after sporozoites had invaded hepatocytes, mAb NYLS3 eliminated P. yoelii infected hepatocytes from culture (Table 1, Exp. 1 and 2). The highest level of inhibition (98%) was obtained when NYLS3 was added to the cultures 24 hours after sporozoite inoculation, and was further incubated for a total of 48 hours. Incubation of NYLS3 with sporozoites and hepatocytes for shorter periods (0–3 hours or 3–24 hours) produced a slightly lower level of inhibition (90% and 95% respectively). To demonstrate the stage specificity of inhibitory activity, the assay was conducted with NYS1, a mAb that recognizes the P. yoelii CSP (Charoenvit et al., 1987), and inhibits sporozoite invasion of hepatocytes in vitro (Charoenvit et al., 1991b). This mAb had greater inhibitory activity than NYLS3 when incubated with sporozoites prior to their invasion (0–3 hours), but significantly less activity when added after sporozoites had invaded hepatocytes (3–24 or 24–48 hours) (Table 1, Exp. 1). NYLS3 clearly demonstrated an inhibitory effect on the infected hepatocytes after sporozoites have invaded. To demonstrate the species-specific inhibitory activity of NYLS3, the ILSDA was conducted with the closely related rodent malaria parasite, P. berghei. NYLS3 had no inhibitory activity against P. berghei-infected hepatocytes (Table 1, Exp. 3).

TABLE 1 mAb NYLS3 eliminates P. yoelii liver schizonts, but not P. berghei liver schizonts from cultures

| MAbs | # Schizonts/culture[a] | | |
|---|---|---|---|
| | 0–3 h[b] | 3–24 h[b] | 24–48 h[b] |
| Exp. 1: P. yoelii | | | |
| NYLS3 (IgG1) | 15.67 ± 4.73 | 5.33 ± 1.53 | 3.00 ± 0 |
| Tryp[c] (IgG1) | 162.33 ± 37.75 (90%) | 106.00 ± 11.27 (95%) | 126.00 ± 16.82 (98%) |
| NYS1 (igG3) | 0.67 ± 0.58 | 77.67 ± 13.87 | 74.33 ± 1.53 |
| NvS3[d] (IgG3) | 169.33 ± 39.72 (99.6%) | 109.00 ± 28.69 (28%) | 97.00 ± 45.57 (24%) |
| Exp. 2: P. yoelii | | | |
| NYLS3 (IgG1) | 14.00 ± 4.36 | ND | 5.33 ± 1.53 |
| NFS1[e] (IgG1) | 46.67 ± 9.71 (70%) | ND | 62.33 ± 15.53 (94%) |
| Exp. 3: P. berghei | | | |
| NYLS3 (IgG1) | ND | ND | 423.33 ± 93.19 |
| NFS1 (IgG1) | ND | ND | 373 ± 69.48 (0%) |

[a]Mean number of liver schizonts in triplicate cultures ± SD.
[b]Sporozoites were added to hepatocyte cultures at 0 hours. The mAbs were incubated with hepatocyte cultures from 0 to 3 hours, from 3 to 24 hours and from 24 to 48 hours.
[c]Anti-*Trypanosoma rhodesiense* mAb, a control for NYLS3.
[d]Anti-*P. vivax* CSP mAb, a control for NYS1.
[e]Anti-*P. falciparum* CSP mAb, another control for NYLS3.

Passive immunization

To determine if the mAb had activity against infected hepatocytes in vivo, mice were first injected i.v. with $5 \times 10^5$ P. yoelii sporozoites. At 3 and 24 hours after sporozoite inoculation, mice were injected i.v. with 2.5 mg NYLS3 in PBS, NFS1 in PBS, or PBS alone. The livers were examined 43 hours after sporozoite inoculation for the presence of liver stage parasites.

When compared to PBS, NYLS3 reduced the numbers of liver schizonts by 35.1% (16.8±2.3 vs 10.9±2.3 schizonts/ 2.5×10$^5$ hepatocytes) in experiment 1, and 46.4% (18.7±2.0 vs 10.0±5.6/2.5×10$^5$ hepatocytes) in experiment 2 (p<0.05, Wilcoxon ranked sum test). When compared to a control mAb (NFS1), NYLS3 reduced the number of liver schizonts by 27.8% (15.1±1.6 vs 10.0±2.3/2.5×10$^5$ hepatocytes) and 10.7% (11.2±9.4 vs 10.0±5.6/2.5×10$^5$ hepatocytes) in two experiments respectively, but the differences did not reach the level of statistical significance (p>0.05).

To determine if NYLS3 would protect against challenge in vivo, mice that had received NYLS3 in passive transfer were challenged by i.v. inoculation of 100 *P. yoelii* sporozoites or 200 *P. yoelii* infected erythrocytes. None of the mice that received NYLS3 were completely protected against challenge with either sporozoites or infected erythrocytes. However, when compared with mice that received the control mAb (NFS1, IgG1), the mice that received NYLS3 had a delay in onset of parasitemia, and a reduction in the level of parasitemia within the first five days after challenge with either sporozoites or infected erythrocytes (Table 2). By day 6 there was no difference in the level of parasitemia among these groups of mice (data not shown).

formed with the following amplifiers (Lisa1 and Lisa Ex2) using oligo-dT primed 1st strand cDNA as the template: Lisa1, 5'-GGA ATT CAT GAA AAT CAA TATA AGC T-3'Seq. I.D. No 7; Lisa Ex2, 5'-GGG ATC CTG ATT TGC CAA TTT GAA A-3'Seq. I.D. No 8. The amplified DNA fragment was digested with EcoRI and BamHI, then cloned into like-digested plasmid pUC18 to obtain pUC18/ LisaEx1.2. The cDNA sequence was derived from the cloned PCR fragment in pUC18/LisaEx1.2 by DNA sequence determination from alkaline-denatured double-stranded templates as described (Sambrook et al.).

Results

An immunoreactive λ 11 clone designated Lisa3 was selected based on its recognition by the monoclonal anti-HEP17 antibody NYLS3. The DNA sequence and the possible open reading frames (deduced peptide sequences) for this orientation of the plasmodial DNA of Lisa3 clone are shown in Seq. ID #5. Striking amino acid sequence identity was found between one of these opening reading frames of the Lisa3 sequence (Seq. ID #5, 692–1111) and a region of the peptide sequence of the Exp1 antigen from *P. falciparum* (Hope et al., 1985) [PfExp1(ID PFAG51ER)]: between bases 776–994 (Seq. ID #5) a 73 amino acid (AA) stretch

TABLE 2

Infection and parasite density in mice after passive transfer of NYLS3 and challenge with 100 *P. yoelii* sporozoites or 200 *P. yoelii* infected erythrocytes

| | Treatment | | | | | |
|---|---|---|---|---|---|---|
| | Days after sporozoite challenge | | | Days after blood stage challenge | | |
| | 3 | 4 | 5 | 3 | 4 | 5 |
| A. Number of mice infected/number of mice tested | | | | | | |
| NYLS3 | 0/10 | 1/10$^a$ | 10/10 | 0/10$^b$ | 8/10 | 10/10 |
| NFS1 | 0/9 | 5/9 | 9/9 | 7/10 | 10/10 | 10/10 |
| PBS | 0/10 | 6/10 | 10/10 | 3/10 | 10/10 | 10/10 |
| B. Mean % parasitemia × 10$^{-3}$ (95% C.I.) | | | | | | |
| NYLS3 | 0 | 0.3 (0–1) | 34 (5–63) | 0 | 22 (10–34) | 434 (249–619) |
| NFS1 | 0 | 3 (1–5) | 120 (24–216) | 4 (1–7) | 56 (32–80) | 895 (647–1143) |
| PBS | 0 | 5 (0.1–9.5) | 195 (47–343) | 2 (0–3) | 56 (32–80) | 895 (647–1143) |

$^a$Frequency of infection in NYLS3 group versus NFS1 group (p = 0.057, Fisher's exact test, two tailed)
$^b$Frequency of infection in NYLS3 group versus NFS1 group (p = 0.003, Fisher's exact test, two tailed)

Example 2

Characterization of the HEP17 gene of *Plasmodium yoelii*

Materials and Methods

*P. yoelii* 17X (NL) parasite DNA was prepared from BALB/c mouse parasitized erythrocytes as described previously (Wortman et al.). A *P. yoelii* λ 11 genomic expression library was constructed and screened for antigen-expressing clones with monoclonal antibody as previously described (Hedstrom et al., 1990). The monoclonal antibody used, NYLS3, is described above in Example 1 (Charoenvit et al.). The derived genomic DNA sequence of the plasmodial DNA from immunoreactive clones was determined by using a commercial DNA sequencing kit (Sequenase, USB, Cleveland, Ohio) with single stranded templates generated via M13 clones. The clone recognized by NYLS3 is called Lisa3 clone and the gene isolated from this clone is called PyHEP17 gene.

Reverse transcription-polymerase chain reaction (RT-PCR) amplification of cDNA from blood stage parasite mRNA, performed essentially as previously described (Hedstrom et al., 1989) for sporozoite mRNA, was per-displayed 59% amino acid sequence identity with the corresponding region of PfExp1. This region was localized to exon 2 of PfExp1 [Simmons et al., (ID PFEXP1G)]. This discovery was the first suggestion that PyHEP17 is the *P. yoelii* homologue of PfExp1. No other strikingly homologous regions were observed, but an open reading frame of similar size to exon 1 of PfExp1 and distance from the putative exon 2 of the Lisa3 clone was detected and it contained an ATG codon at base 378 (Seq. ID #5).

To determine whether these were indeed exons, a cDNA clone, designated pUC18/LisaEx1.2, was isolated from blood stage parasite mRNA via RT-PCR. The oligonucleotide primers for the amplification were predicted from the Lisa3 clone sequence to amplify a cDNA that would include all of the putative exon 1 beginning with the initiation ATG and that portion of putative exon 2 homologous to PfExp1. The cDNA sequence of clone pUC18/LisaEx1.2 and the derived amino acid of this cDNA is shown in FIG. 8.

The alignment shown in FIG. 7 demonstrated 47% deduced amino acid homology of this not yet full-length cDNA with that of the overlapping region of PfExp1, which is clearly indicative of relatedness. Further examination of the Lisa3 genomic DNA sequence (Seq. ID #5) predicted that the level of inferred peptide relatedness between PfExp1 and PyHEP17 (Charoenvit et al. submitted for publication) will exceed 47% amino acid sequence identity.

Example 3

P. yoelii Hepatocyte Erythrocyte Protein 17 (PyHEP17)

Construction of nkCMVintPolyli/LisaEx1.2 DNA vaccine

A DNA vaccine consisting of exon 1 (121 bp) and 65% of exon 2 (221 bp) of PyHEP17, not including the region of the PyHEP17 protein recognized by NYLS3, cloned into the nkCMVintPolyli vector, the expression of which is driven by a Cytomegalovirus promoter, was constructed as follows. The pUC18/LisaEx1.2 cDNA clone was digested with HindIII and ECoR1 restriction enzyme to release the cDNA fragment. The pBluescript SK+ vector was similarly digested with HindIII and ECoR1. The LisaEx1.2 insert was directionally ligated into pBluescript SK+. Selected colonies were purified and digested with restriction enzymes, and the DNA sequence of colonies with the correct restriction enzyme pattern was determined from alkaline denatured double-stranded templates to confirm the cDNA sequence (pSK+/LisaEx1.2 plasmid). The pBluescript SK+ plasmid containing exon 1 and 65% of exon 2 of PyHEP17 was digested with PstI restriction enzyme to release the cDNA fragment. The nkCMVintPolyli vector was similarly digested with Pst1 and treated with calf intestinal phosphatase enzyme to reduce the background of relegated vector without insert. The cDNA insert was ligated into nkCMVintPolyli and host cells transformed.

Selected colonies were further screened and digested. The insert DNA sequence of plasmid DNA isolated from colonies with the correct restriction enzyme pattern was determined from alkaline denatured double-stranded templates to confirm the LisaEx1.2 cDNA sequence (nkCMVintPolyli/LisaEx1.2 plasmid). Large-scale quantities of the nkCMVintPolyli/LisaEx1.2 plasmid and a control plasmid nkCMVintPolyli were prepared by the alkaline lysis method and purified by banding and rebanding on cesium chloride gradients. Plasmid DNA was resuspended at a final concentration of 2 mg/ml in sterile saline and stored at −70° C. Agarose gel electrophoresis of undigested and restriction enzyme digested plasmids followed by ethidium bromide staining revealed that the majority of plasmid was present in a super-coiled form and yielded fragments of the predicted size upon digestion (data not shown). The $A_{260}/A_{280}$ ratios of 1.88–1.94 indicated that the plasmid preparations were pure.

nkCMVintPolyli/LisaEx1.2 DNA vaccine-induced protection

To test the DNA construct as a vaccine, mice of each of the strains BALB/c ($H-2^d$), C57 BL/6 ($H-2^b$), B10.BR ($H-2^k$), B10.Q ($H-2^q$), and A/J ($H-2^a$) were immunized intramuscularly in each tibialis anterior muscle with three doses of 200 μg/100 μl nkCMVintPolyli/LisaEx1.2 DNA vaccine per mouse at three week intervals. Mice of each of the strains were immunized with the control nkCMVintPolyli plasmid. Serum was collected from all mice between each immunization, and was tested for recognition of air-dried liver-stage and blood-stage P. yoelii parasites by the indirect fluorescent antibody test (IFAT).

Two weeks after the third immunization, mice were challenged with 100 infectious P. yoelii sporozoites (>50 $ID_{50}$). Since the $ID_{50}$ for P. yoelii in mice is often less than two sporozoites, this represents a significant challenge. Blood smears were collected from day 4 to day 14 following challenge, stained with Giemsa, and the development of blood-stage parasitemia monitored. Protection was defined as the complete absence of blood-stage parasitemia.

Antibodies induced by the nkCMVintPolyli/LisaEx1.2 DNA vaccine recognized both liver-stage and blood-stage P. yoelii parasites, as demonstrated by IFAT. Both liver-stage specific and blood-stage-specific antibody titres were low and not all mice developed blood-stage antibody titres, even after 3 immunizations. Some sera which recognized P. yoelii liver-stage parasites did not recognize P. yoelii blood-stage parasites, and some sera which recognized P. yoelii blood-stage parasites showed little recognition of P. yoelii liver-stage parasites. These data indicate that there may be two distinct B cell epitopes present on the region of the gene encoding exon 1 and 65% of exon 2 of the HEP17 protein, one epitope being preferentially recognized by liver-stage parasites, and the other by blood-stage parasites. This DNA vaccine construct does not include the region of the PyHEP17 protein recognized by the NYLS3 mAb. Sera from mice immunized with the control plasmid, nkCMVintPolyli, did not recognize either liver-stage or blood-stage P. yoelli parasites.

Following challenge, 86% of the A/J mice, 33%–43% of the B10.BR mice, 14%–20% of the B10.Q mice, and 17%–29% of the Balb/c mice were completely protected against development of blood-stage parasitemia (TABLE 3). C57 BL/6 mice were not protected. Furthermore, a delay in the onset of parasitemia was observed in some mice which were not protected. The onset of parasitemia was delayed for 4–6 days in 14–17% of the BALB/c mice and for 4 days in 17% of the B10.BR mice, indicating that the DNA vaccine was having an effect even in mice which were not solidly protected against challenge.

Although the highest levels of antibodies (both liver-stage and blood-stage specific) were observed in C57 BL/6 mice, these mice were not protected against development of blood-stage parasitemia, nor was the onset of parasitemia delayed. Furthermore, there was no apparent correlation between levels of liver-stage or blood-stage specific antibodies and protection against development of blood-stage parasitemia in the other mouse strains. Data suggest that T-cell mediated immune responses specific for PyHEP17 may play a role in the DNA vaccine-induced protection.

This LisaEx1.2 DNA vaccine did not protect mice against challenge with 200 infected erythrocytes, as assessed when the mice protected against sporozoite challenge were rechallenged. This indicates that the protective immunity induced by the DNA vaccine is targeted at the infected hepatocyte. The low antibody titres, both liver-stage and blood-stage specific, induced by this DNA vaccine support this hypothesis. The antibody levels in the A/J mice, 86% of which were protected, were very low (<1/40), and the C57 BL/6 mice which were not protected had the highest antibody titres (<1/640). Also, the class I haplotype of the A/J mice, H-2a, represents both the H-2k haplotype of the B10.BR mice, and the H-2d haplotype of the BALB/c mice. The greater protection noted with the A/J mice (86%) may therefore represent additive protection mediated by H-2k and H-2d class I restricted T cell responses. Data indicates that T cell-mediated immune responses specific for PyHEP17 may play a role in the DNA vaccine-induced protection.

Example 4

Combination DNA vaccine (nkCMVintPolyli/LisaEx1.2 DNA vaccine plus nkCMVintPolyli/CSP DNA vaccine) induced protection Mice were immunized intramuscularly with 100 ug/mouse of the nkCMVintPolyli/LisaEx1.2 DNA vaccine plus 40 ug/mouse of a nkCMVintPolyli/CSP DNA vaccine. These vaccines were administered together at the same time in the same sites. Five strains of mice differing in their class I MHC haplotypes [A/J ($H-2^a$), B10.BR ($H-2^k$), BALB/c ($H-2^d$), B10.Q ($H-2^q$) and C57 BL/6 ($H-2^b$)] were immunized, using the same regime described previously for the nkCMVintPolyli/LisaEx1.2 DNA vaccine (i.e 3 immunizations I.M. at 3 week intervals). Mice were challenged with 100 infectious *P. yoelii* sporozoites.

This combination of the nkCMVintPolyli/LisaEx1.2 DNA vaccine plus a nkCMVintPolyli/CSP DNA vaccine was able to confer complete protection againt *P. yoelii* sporozoite challenge in one mouse strain and additive protection in two strains (TABLE 4) 100% of BALB/c mice immunized with the combination of DNA vaccines were protected. Only 86% of BALB/c mice immunized with the CSP vaccine and 29% of BALB/c mice immunized with the LisaEx1.2 vaccine were protected. Furthermore, 71% of B10.BR immunized with the combination of DNA vaccines were protected. Only 20% of B10.BR mice immunized with the CSP vaccine and 43% of B10.BR mice immunized with the LisaEx1.2 vaccine were protected. This data indicate that the protection conferred by this combination of DNA vaccines is additive.

Although no C57 BL/6 mice and few B10.Q mice were protected, a delay in the onset of parasitemia was nevertheless observed in some mice which were not protected. A delay of 2–3 days was noted in 29% of the C57 BL/6 mice and of 6 days in 14% of the B10.Q mice, indicating that even in those mice which were not protected, the combined DNA vaccines were having an effect.

TABLE 3

Summary: Lisa Ex 1.2 DNA vaccine - induced protection

|  | Lisa Ex 1.2 (Expt 1) | Lisa Ex 1.2 (Expt 2) |
| --- | --- | --- |
| A/J | n.t. | 86% (6/7) |
| B10.BR | 33% (2/6) | 43% (3/7) |
| BALB/c | 17% (1/6) | 29% (2/7) |
| B10.Q | 20% (1/5) | 14% (1/7) |
| C57 BL/6 | 0/6 (0%) | 0/7 (0%) |

TABLE 4

Summary: combined DNA vaccine - induced protection

|  | Lisa Ex 1.2 only | CSP Only | Lisa Ex 1.2 + CSP |
| --- | --- | --- | --- |
| BALB/c | 29% (2/7) | 86% (6/7) | 100% (7/7) |
| A/J | 86% (6/7) | 43% (3/7) | 71% (5/7) |
| B10.BR | 43% (3/7) | 20% (1/5) | 71% (5/7) |
| B10.Q | 14% (1/7) | 0% (0/7) | 14% (1/7) |
| C57 BL/6 | 0/7 (0%) | 0% (0/7) | 0% (0/7) |

Many modifications and variations of the present invention are possible in light of the above teachings. It is therefore to be understood that, within the scope of the appended claims, the invention may be practiced otherwise than as specifically described.

REFERENCES

Atkinson, C. T., P. Millet, W. E. Collins, and M. Aikawa. 1989. Localization of circumsporozoite antigen in exoerythrocytic schizonts of *Plasmodium cynomolgi. Am. J. Trop. Med. Hyg.* 40:131.

Chang, S. P., H. L. Gibson, C. T. Lee-Ng, P. J. Barr, and G. S. N. Hui. 1992. A carboxy terminal fragment of Plasmodium gp 195 expressed by a recombinant baculovirus induced antibodies that completely inhibit parasite growth. *J. Immunol.* 149:548.

Charoenvit, Y., M. F. Leef, L. F. Yuan, M. Sedegah, and R. L. Beaudoin. 1987. Characterization of *Plasmodium yoelii* monoclonal antibodies directed against stage-specific sporozoite antigens. *Infect. Immun.* 55:604.

Charoenvit, Y., S. Mellouk, C. Cole, R. Bechara, M. F. Leef, M. Sedegah, L. F. Yuan, F. A. Robey, R. L. Beaudoin, and S. L. Hoffman. 1991a. Monoclonal, but not polyclonal, antibodies protect against *Plasmodium yoelii* sporozoites. *J. Immunol.* 146:1020.

Charoenvit, Y., W. E. Collins, T. R. Jones, P. Millet, L. Yuan, G. H. Campbell, R. L. Beaudoin, and S. L. Hoffman. 1991b. Inability of malaria vaccine to induce antibodies to a protective epitope within its sequence. *Science.* 251:668.

Daly, T. M., and C. A. Long. 1993. A recombinant 15-kilodalton carboxyl-terminal fragment of *Plasmodium yoelii* 17XL merozoite surface protein 1 induces a protective immune response in mice. *Infect. Immun.* 61:2462.

Dame, J. B., J. L. Williams, T. F. McCutchan, J. L. Weber, R. A. Wirtz, W. T. Hockmeyer, W. L. Maloy, J. D. Haynes, I. Schneider, D. Roberts, G. S. Sanders, E. P. Reddy, C. L. Diggs, and L. H. Miller. 1984. Structure of the gene encoding the immunodominant surface antigen on the sporozoite of the human malaria parasite *Plasmodium falciparum. Science.* 225:593.

Danforth, H. D., G. H. Campbell, M. F. Leef, and R. L. Beaudoin. 1982. Production of monoclonal antibodies by hybridomas sensitized to sporozoites of *Plasmodium berghei. J. Parasitol.* 68:1029.

Ey, P. L., S. J. Prowse, and C. R. Jenkin. 1978. Isolation of pure IgGI, IgG2a, and IgG2b immunoglobulins from mouse serum using protein A sepharose. *Immunochemistry.* 15:429.

Guerin-Marchand, C., P. Druilhe, B. Galey, A. Londono, J. Patarapotikul, R. L. Beaudoin, C. Dubeaux, A. Tartar, O. Mercereau-Puijalon, and G. Langsley. 1987. A liver-stage-specific antigen of *Plasmodium falciparum* characterized by gene cloning. *Nature* (London) 329:164.

Hedstrom, R. C. et al. 1990. A malaria sporozoite surface antigen distinct from the circumsporozoite protein. *Bull. WHO* (Suppl.) 68, 152–157.

Hedstrom, R. C., J. R. Campbell, M. L. Leef, Y. Charoenvit, M. Carter, M. Sedegah, R. L. Beaudoin and S. L. Hoffman. 1990. A malaria sporozoite surface antigen distinct from the circumsporozoite protein. *WHO. Bull. Suppl.* 68:152.

Hoffman, S. L., D. Isenbarger, G. W. Long, M. Sedegah, A. Szarfman, L. Waters, M. R. Hollingdale, P. H. Van der Meide, D. S. Finbloom, and W. R. Ballou. 1989. Sporozoite vaccine induces genetically restricted T cell elimination of malaria from hepatocytes. *Science.* 244:1078.

Hoffmnan, S. L., E. D. Franke, W. O. Rogers, and S. Mellouk. 1993. Preerythrocytic malaria vaccine development. In *Molecular immunological considerations in malaria vaccine development.* M. F. Good and A. J. Saul, eds. CRC Press, Boca Raton, Fla. p.149.

Holder, A. A., and R. R. Freeman. 1984. The three major antigens on the surface of *Plasmodium falciparum* merozoites are derived from a single high molecular precursor. *J. Exp. Med.* 160:624.

Hope, I. A. et al. 1985. The gene for an exported antigen of the malaria parasite *Plasmodium falciparum* cloned and expressed in *Escherichia coli. Nucleic Acids Res.* 13, 369–379.

Jiao, S. et al. (1992) Direct Gene Transfer into Nonhuman Primate Myofibers *In Vivo. Human Gene Therapy.* 3:21–33.

Khusmith, S., M. Sedegah, and S. L. Hoffman. 1994. Complete protection against *Plasmodium yoelii* by adoptive transfer of a CD8+ cytotoxic T cell clone recognizing sporozoite surface protein 2. *Infect. Immun.* 62:2979.

Khusmith, S., Y. Charoenvit, S. Kumar, M. Sedegah, R. L. Beaudoin, and S. L. Hoffman. 1991. Protection against malaria by vaccination with sporozoite surface protein 2 plus CSP. *Science.* 252:715.

Laemmli, U. K. 1970. Cleavage of structural proteins during the assembly of the head of bacteriophage T4. *Nature (London).* 227:680.

Mellouk, S., N. Berbiguier, P. Druilhe, M. Sedegah, B. Galey, L. Yuan, M. Leef, Y. Charoenvit, C. Paul, S. L. Hoffman, and R. L. Beaudoin. 1990. Evaluation of an in vitro assay aimed at measuring protective antibodies against sporozoites. *WHO Bull.* Suppl. 68:52.

Nussenzweig, R. S. et al., Malaria Vaccines: Multiple Targets, Science 265: 1381–1383 (1994).

Pacheco, N. D., C. P. A. Strome, F. Mitchell, M. P. Bawden, and R. L. Beaudoin. 1979. Rapid, large-scale isolation of *Plasmodium berghei* sporozoites from infected mosquitoes. *J. Parasitol.* 65:414.

Potocnjak, P., N. Yoshida, R. S. Nussenzweig, and V. Nussenzweig. 1980. Monovalent fragments (Fab) of monoclonal antibodies to sporozoite surface antigen (Pb 44) protect mice against malaria infection. *J. Exp. Med.* 151:1504.

Rodrigues M., R. S. Nussenzweig, P. Romero, and F. Zavala. 1992. The in vivo cytotoxic activity of CD8+ T cell clones correlates with their levels of expression of adhesion molecules. *J. Exp. Med.* 175:895.

Rogers, W. O., A. Malik, S. Mellouk, K. Nakamura, M. D. Rogers, A. Szarfman, D. M. Gordon, A. K. Nussler, M. Aikawa, and S. L. Hoffman. 1992. Characterization of *Plasmodium falciparum* sporozoite surface protein 2. *Proc. Natl. Acad. Sci. USA.* 89:9176.

Rogers, W. O., M. D. Rogers, R. C. Hedstrom, and S. L. Hoffman. 1992. Characterization of the gene encoding sporozoite surface protein 2, a protective *Plasmodium yoelii* sporozoite antigen. *Mol. Biochem. Parasitol.* 53:45.

Romero, P., J. L. Maryanski, G. P. Corradin, R. S. Nussenzweig, V. Nussenzweig, and F. Zavala. 1989. Cloned cytotoxic T cells recognize an epitope in the circumsporozoite protein and protect against malaria. *Nature.* 341:323.

Sambrook, et al. *Molecular cloning, a laboratory manual,* second edition. Cold Spring Harbor, Cold Spring Harbor Laboratory, 1989.

Sanchez, G. I., W. O. Rogers, S. Mellouk, and S. L. Hoffman. 1994. *Plasmodium falciparum:* exported protein-1, a blood stage antigen is expressed in liver stage parasites. *Exp. Parasitol.* In press.

Sedegah, M. et al. 1994. Protection against malaria by immunization with circumsporozoite protein plasmid DNA. PNAS (in press).

Simmons, D. et al. 1987. A malaria protein exported into a new compartment within the host erythrocyte. *EMBO J.* 6, 485–491.

Sinden, R. E., A. Couchman, A. Suhrbier, F. Marsh, L. Winger, and G. Ranawaka. 1991. The development of exo-erythrocytic schizonts of *Plasmodium berghei* in vitro from gamma-irradiated and non-irradiated sporozoites: a study using confocal laser scanning microscopy. *Parasitology* 103:17.

Szarfman, A., J. A. Lyon, D. Walliker, I. Quakyi, R. J. Howard, S. Sun, W. R. Ballou, K. Esser, W. T. London, R. A. Wirtz, and R. Carter. 1988. Mature liver stages of cloned *Plasmodium falciparum* share epitopes with proteins from sporozoites and asexual blood stages. *Parasite Immunol.* 10:339.

Towbin H., T. Staehelin, and J. Gordon. 1979. Electrophoretic transfer of proteins from polyacrylamide gels to nitrocellulose sheets: procedures and some applications. *Proc. Natl. Acad. Sci. USA.* 76:4350.

Wang, B. et al. 1993. DNA Inoculation Induces Neutralizing Immune Responses Against Human Immunodeficiency Virus Type 1 in Mice and Nonhuman Primates. *DNA and Cell Biology.* 12:799–805.

Weiss, W. R., J. A. Berzofsky, R. A. Houghten, M. Sedegah, M. Hollingdale, and S. L. Hoffman. 1992. A T cell clone directed at the circumsporozoite protein which protects mice against *Plasmodium yoelii* and *Plasmodium berghei. J. Immunol.* 149:2103.

Weiss, W. R., M. Sedegah, R. L. Beaudoin, L. H. Miller, and M. F. Good. 1988. CD8+ T cells (cytotoxic/suppressors) are required for protection in mice immunized with malaria sporozoites. *Proc. Natl. Acad. Sci. USA.* 85:573.

Wortman, A. et al. 1989. Cloning of *P. yoelii* genes expressing three different sporozoite-specific antigens. *Micro. Path.* 6, 227–231.

Zhu, J., and M. Hollingdale. 1991. Structure of *Plasmodium falciparum* liver stage antigen-1. *Mol. Biochem. Parasitol.* 48:223.

---

What is claimed is:

1. A vaccine for protecting a mammal by reducing the severity or incidence of infection by a malaria parasite of the genus Plasmodium, said vaccine comprising a first nucleic acid encoding a first polypeptide capable of eliciting an immune reaction against an antigen expressed during the liver stage and wherein said first nucleic acid comprises the nucleotide sequence encoding the homologue of PyHEP17 in other Plasmodium species selected from the group consisting of *Plasmodium falciparum, Plasmodium vivax, Plasmodium ovale,* and *Plasmodium malariae.*

2. The vaccine of claim 1, wherein said mammal is a human.

3. The vaccine of claim 1, wherein said malaria parasite is *Plasmodium falciparum.*

4. The vaccine of claim 3, wherein said nucleic acid encodes an antigenic fragment of the protein PyHEP17.

5. The vaccine of claim 4, wherein said antigenic fragment consists of the homolog of an amino acid sequence selected from the group consisting of SFPMNEESPLGF-SPE (Seq. I.D. No 1), EESPLGFSPEEMEAV (Seq. I.D. No 2), EESPLGFSPE (Seq. I.D. No 9), and the polypeptide having the amino acid sequence as shown in FIG. 8 (Seq. I.D. No 4).

6. The vaccine of claim 3, further comprising at least a second DNA fragment encoding a second polypeptide capable of eliciting an immune reaction against an antigen expressed during at least one stage of malaria infection selected from the group consisting of the sporozoite stage, liver stage and the blood stage.

7. The vaccine of claim 6, wherein said first DNA fragment is from the species *Plasmodium falciparum.*

8. The vaccine of claim 6, wherein said second DNA fragment is selected from the group consisting of DNA that encodes circumsporozoite protein of *Plasmodium yoelii,* and DNA that encodes a homolog of the circumsporozoite protein in other Plasmodium species selected from the group consisting of *Plasmodium falciparum, Plasmodium vivax, Plasmodium malariae,* and *Plasmodium ovale.*

9. The vaccine of claim 6, wherein said second DNA fragment encodes the circumsporozoite protein of *Plasmodium falciparum.*

10. A composition for stimulating an immune response against infection by a Plasmodium species in a mammal, said composition comprising a first DNA fragment of said Plasmodium species encoding a homolog of the protein PyHEP17, wherein said Plasmodium species is selected from the group consisting of *Plasmodium falciparum, Plasmodium vivax, Plasmodium malariae,* and *Plasmodium ovale*; and a second DNA of Plasmodium species encoding at least one protein selected from the group consisting of the known *P. falciparum, P. vivax, P. malariae,* and *P. ovale* CSP; SSP2(TRAP); Pfs16 (Sheba); LSA-1; LSA-2; LSA-3; STARP; MSA-1 (MSP-1, PMMSA, PSA, p185, p190); MSA-2 (MSP-2, Gymmsa, gp56, 38–45 kDa antigen); RESA (Pf155); EBA-175; AMA-1 (Pf83); SERA (p113, p126, SERP, Pf140); RAP-1; RAP-2; RhopH3; PfHRP-II; Pf55; Pf35; GBP (96-R); ABRA (p101); Exp-1 (CRA, Ag5.1); Aldolase; Duffy binding protein of *P. vivax*; Reticulocyte binding proteins; HSP70-1 (p75); Pfg25; Pfg28; Pfg48/45; and Pfg230, wherein said first and second DNA fragments are formulated as a vaccine in a pharmaceutically effective carrier.

11. A method of protecting a mammalian subject against infection by malaria caused by Plasmodium species selected from the group consisting of *Plasmodium falciparum* and *Plasmodium vivax,* said method comprising administering to said mammal the vaccine of claim 1.

* * * * *